United States Patent [19]

Tanabe et al.

[11] Patent Number: 5,389,538
[45] Date of Patent: Feb. 14, 1995

[54] MUTANT HUMAN PROUROKINASE

[75] Inventors: Toshizumi Tanabe; Masanori Morita; Masaaki Hirose; Yasuo Amatsuji, all of Hirakata, Japan

[73] Assignee: The Green Cross Corporation, Osaka, Japan

[21] Appl. No.: 957,039

[22] Filed: Oct. 6, 1992

[30] Foreign Application Priority Data

Oct. 7, 1991 [JP] Japan .................................. 3-289257

[51] Int. Cl.⁶ ...................... A61K 37/547; C12N 9/72
[52] U.S. Cl. .................................. 435/215; 424/94.64
[58] Field of Search ............................... 435/194, 215

[56] References Cited

U.S. PATENT DOCUMENTS 5,098,840  3/1992  Kasai et al. ......................... 435/215

OTHER PUBLICATIONS

*Proc. Natl. Acad. Sci. USA,* "A GAL 10-CYC1 hybrid yeast promoter identifies the GAL4 regulatory region as an upstream site", Leonard Guarente et al., vol. 79, pp. 7410–7414, Dec. 1982.
Sobel, B. E. et al., Circulation 81:1362–1373 (1990).
Pierard, L. et al., J. Biotechnol. 15:283–304 (1990).
Lehninger, A. L., Principles of Biochemistry, Worth Publishers, Inc., New York (1982), pp. 100–108.
Hiramatsu, R. et al., Gene 99:235–241 (1991).
Li, X. K. et al., Biochim. Biophys. Acta 1159:37–43 (1992).
Lisnen, H. R. et al., Eur. J. Biochem. 205:701–709 (1992).

*Primary Examiner*—Robert A. Wax
*Assistant Examiner*—Eric Grimes
*Attorney, Agent, or Firm*—Sugrue, Mion, Zinn, Macpeak & Seas

[57] ABSTRACT

A mutant human prourokinase wherein a neutral amino acid in the epidermal growth factor (EGF) region of human prourokinase (human PUK) has been replaced with a basic amino acid, or an acidic amino acid has been replaced with a non-acidic amino acid, and a method for producing a mutant human PUK which comprises expression of mutant human PUK by cultivating a host transformed by a plasmid inserted with a DNA sequence coding for said mutant human PUK. By replacing a neutral amino acid in the EGF region of human PUK which is a fibrinolysin with a basic amino acid, or an acidic amino acid with a non-acidic amino acid, half-life in blood can be prolonged, and affinity for fibrin can be improved.

1 Claim, 16 Drawing Sheets

```
12      14       16      18      20      22    (Amino Acid No.)
Asp Cys Leu Asn Gly Gly Thr Cys Val Ser Asn
GAC TGT CTA AAT GGA GGA ACA TGT GTG TCC AAC AC TGT CTA AAT AAA GGT ACC TGT GTG TCC AAC
                   Lys  Kpn I

5'-ACTGT CTAAA TAAAG GTACC TGTGT GTCCA AC-3'
```

FIG. 2

```
     32                          38                    43    (Amino Acid No.)
     Asn Cys Pro Lys Lys Phe Gly Gly Gln His Cys Glu
     AAC TGC CCA AAG AAA TTC GGA GGG CAG CAC TGT GAA
     C TGT CCA AAG AAA TTT AAA GGG CAG CAC TGT GA
                     Dra I
                     Lys

5'-CTGCC CAAAG AAATT TAAAG GGCAG CACTG TGA-3'
```

FIG. 6

```
40        42        44        46        48        50        52        54   (Amino Acid No.)
Gln His Cys Glu Ile Asp Lys Ser Lys Thr Cys Tyr Glu Gly Asn
CAG CAC TGT GAA ATA GAT AAG TCA AAA ACC TGC TAT GAG GGG AAT CAG CAC TGT GAA ATT AAT AAG TCA AAA ACA TGT TAT GAG GGG AAT
        Vsp I                        Nsp(7524)I
          Asn
5'-CAGCA CTGTG AAATT AATAA GTCAA AAACA TGTTA TGAGG GGAAT -3'
```

MUTANT HUMAN PROUROKINASE

FIELD OF THE INVENTION

The present invention relates to a mutant human prourokinase obtained by modifying molecular structure of human prourokinase (hereinafter abbreviated as human PUK), a method of production, a DNA sequence coding for said mutant human PUK, a plasmid inserted with said DNA sequence, and a transformant transformed by said plasmid. More specifically, the present invention relates to a series of techniques for providing a mutant human PUK, which comprise replacing an amino acid sequence of a particular gene with other amino acid sequence at a gene level, and expressing said gene by the recombinant DNA technique.

BACKGROUND OF THE INVENTION

As the plasminogen activator involved in fibrinolysis, known are tissue plasminogen activator (t-PA) produced by endothelial cells, and urokinase (UK), of which UK is conventionally well-known as a fibrinolysin. While UK has been normally purified from human urine or culture of human nephrocyte, production of UK by DNA recombination has been recently achieved (EP-A-154272). When used in a large amount, however, UK induces decomposition and activation of various factors inducing coagulation or fibrinolysis, and causes bleeding. The present inventors have already found that inactivated-type human urokinase precursor produced by human nephrocyte [EP-A-139447, J. Biol. Chem., 260, 12377 (1985)]permits, in contrast to UK, thrombolysis without bleeding [Cell Struc. Func., 10, 151 (1985)].

Human PUK has three domains, namely, epidermal growth factor (hereinafter abbreviated as EGF) domain, kringle domain, and enzyme activity domain [Hoppe-Seyler's Z. Physiol. Chem., 363, 1155 (1982)].

Incidentally, there has been heretofore attempted to modify human PUK in an effort to prolong half-life in blood. For example, there have been reported deletion of the entire EGF region (EP-A-253241), deletion of the first or the third loop in the EGF region (EP-A-398361), addition of a sugar chain by way of a specific partial structure obtained by replacing the amino acid in the EGF region (EP-A-398362), and so on.

On the other hand, while an attempt to increase affinity for fibrin can be evidenced by reports made of hybrid protein of UK or tPA with anti-fibrin antibody, and of incorporation of the kringle region of protein having high affinity for fibrin such as plasminogen into tPA or UK, there have been no reports made of an increased affinity for fibrin by an amino acid replacement.

SUMMARY OF THE INVENTION

An object of the present invention is to provide a mutant human PUK by the least modification without deletion of the EGF region, which affords prolonged half-life in blood as achieved by the EGF region-deleted mutant human PUK, improved affinity for fibrin, and other properties substantially the same as those of human PUK, a method of its production, a DNA sequence coding for said mutant human PUK, a plasmid which has been inserted with said DNA sequence, and a transformant.

In view of the above, the present inventors have conducted intensive studies, and found that replacement of a neutral amino acid in the EGF region of human PUK with a basic amino acid, or replacement of an acidic amino acid in the EGF region of human PUK with a non-acidic amino acid can achieve an improved affinity for fibrin as well as prolonged half-life in blood, which resulted in the completion of the present invention.

The present invention relates to a mutant human PUK wherein a neutral amino acid in the epidermal growth factor region of human PUK has been replaced with a basic amino acid, or an acidic amino acid has been replaced with a non-acidic amino acid, and a method for producing the mutant human PUK, which comprises expression of mutant human PUK by cultivating a host transformed by a plasmid inserted with the DNA sequence coding for said mutant human PUK.

BRIEF DESCRIPTION OF THE DRAWINGS

FIG. 2 shows the sequence of SD16 (32 mer) (SEQ ID NO: 1) and the mutation introduced (SEQ ID NO: 2).

FIG. 6 shows the sequence of SD13 (33 mer) (SEQ ID NO: 3) and the mutation introduced (SEQ ID NO: 4).

FIG. 8 shows the sequence of SD30 (45 mer) (SEQ ID NO: 5) and the mutation introduced (SEQ ID NO: 6).

DETAILED DESCRIPTION OF THE INVENTION

In the present invention, each term has the following meaning.

Human PUK consists of 411 amino acids, and the amino acid sequence and DNA sequence thereof are depicted as SEQ ID NO: 7.

The EGF region of PUK is from 10th Asn to 49th Thr. This EGF region consists of three loops. A first loop is from 10th Asn to 19th Cys, a second loop is from 20th Val to 31st Cys, and a third loop is from 33rd Cys to 42nd Cys.

(1) Mutant human PUK

The mutant human PUK of the present invention is either (1) with a neutral amino acid in the EGF region of human PUK having been replaced with a basic amino acid, or (2) with an acidic amino acid in the EGF region of human PUK having been replaced with a non-acidic amino acid.

The neutral amino acid of the above (1) is exemplified by non-charged amino acids such as Gly, Ser, etc., and the basic amino acid is exemplified by Lys, Arg, His, etc.

The acidic amino acid of the above (2) is exemplified by Glu, Asp, etc., and the non-acidic amino acid is exemplified by amide compounds of acidic amino acid, neutral amino acid, basic amino acid, etc. The amide compound of acidic amino acid is exemplified by Ash, Gln, etc.

The replacement is specifically exemplified by Lys in the place of the 16th Gly, Lys in the place of the 38th Gly, and Asn in the place of the 45th Asp.

The replacement is normally performed by deleting an optional amino acid sequence in the EGF domain, and introducing the desired amino acid or amino acid sequence therefor. The methods known as protein engineering such site-directed deletion [Nucl. Acids Res., 11, 1645 (1983)], site-specific mutagenesis, a method comprising treatment with restriction enzyme and synthetic gene, etc. can be used widely for the replacement of amino acid sequences.

Figure 1:
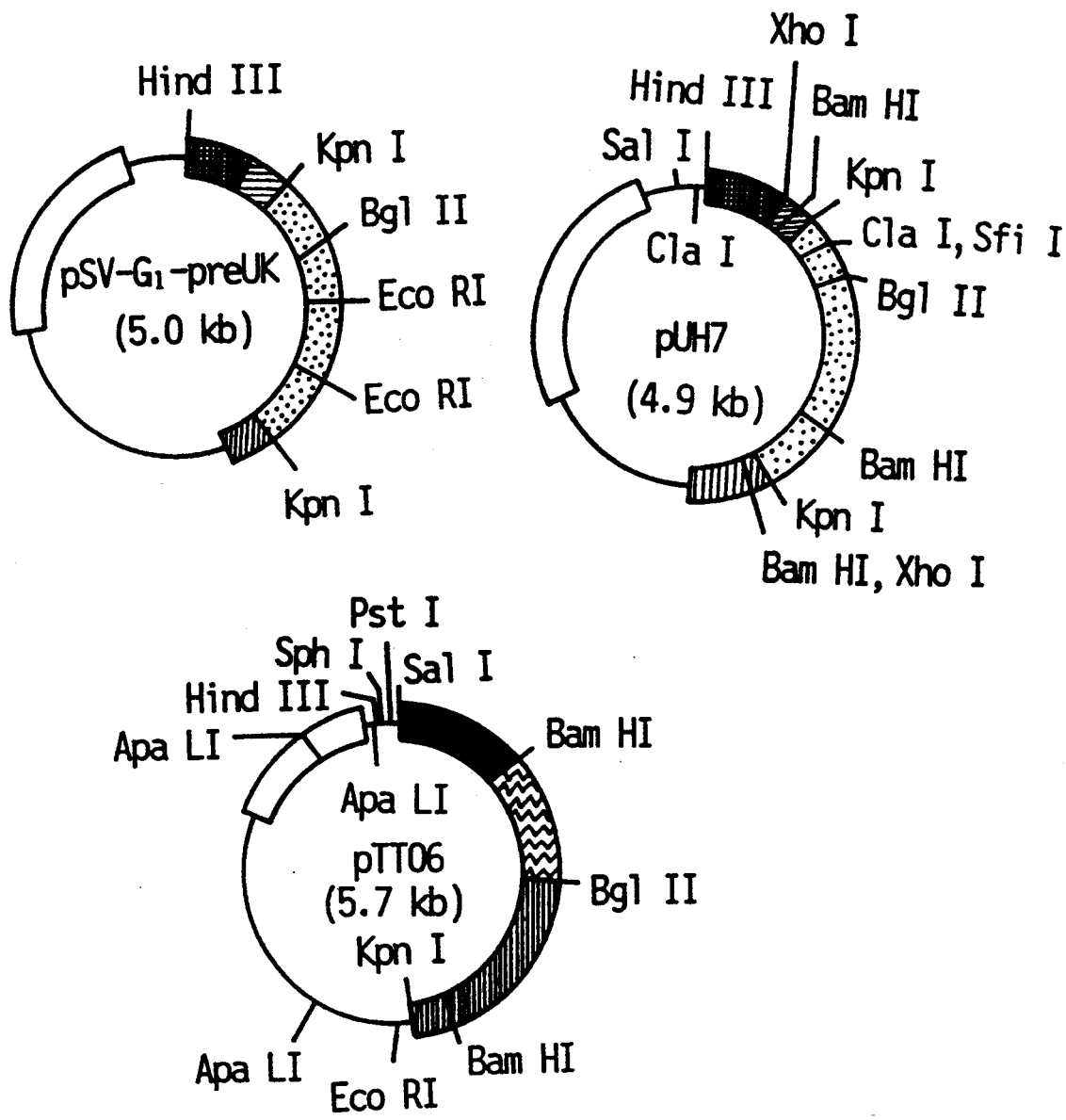
FIG. 1 shows the structures of pSV-G$_1$-preUK, pUH7, and pTT06.

To be specific, the DNA sequence encoding human PUK is used, and such DNA sequence is shown as SEQ ID NO: 7. This DNA can be prepared by the method disclosed in EP-A-154272, EP-A-253241, etc. The plasmid carrying the DNA sequence encoding said human PUK includes pSV-G$_1$-preUK (FIG. 1 or EP-A-154272).

(2) Expression system

The mutant PUK which has been replaced is inserted into an expression vector to construct an expression host-vector. A plasmid vector having a replicon and a control sequence derived from a species convertible with host cells is used in combination with the host. Vectors generally have replication sites, and also marker sequences enabling selection of expression type from among transformant cells.

The method for using *Escherichia coli*, yeasts, *Bacillus subtilis*, or animal cells as a host is disclosed in EP-A-253241. The preferred host is animal cells. Besides the aforementioned EP-A-258241, a method for using animal cells may be a method using amplification by DHFR gene (EP-A-265874), a method wherein the amplification system is reinforced by controlling the DHFR gene with a UK promoter (EP-A-457527), etc.

(3) Concrete expression method

As mentioned earlier, the present invention relates to a method for producing a mutant human PUK which comprises cultivating animal cells transformed by a plasmid inserted with the mutant human PUK gene added with, at its upstream, a promoter capable of controlling expression in animal cells, and the dihydrofolate reductase (DHFR) gene added with a UK promoter, to allow expression of the mutant human PUK.

The present invention will be hereinbelow described in detail.

1. Plasmid

In the present invention, the plasmid has (i) a DNA coding for mutant human PUK added with, at its upstream, a promoter capable of controlling expression in animal cells, and (ii) a DNA coding for dihydrofolate reductase (DHFR) added with a UK promoter at the upstream thereof.

In said plasmid, a promoter capable of controlling expression in animal cells is added upstream of a DNA coding for mutant human PUK to allow the DNA coding for human PUK to act under the control of the promoter capable of controlling expression in animal cells.

The promoter capable of controlling expression in animal cells is derived from polyoma, adenovirus 2, or most frequently-used simian virus 40 (SV40). Early and late SV40 virus promoters are particularly useful, since they can be easily obtained from the virus as fragments containing replication origin of SV40 [Fiers et al. Nature, 273, 113 (1978)]. The fragment containing from HindIII site to the replication origin BglI site of the virus (about 250 bp) can be also used. Promoters and enhancers related to the objective gene can be also used if they are convertible with the host.

The promoter-enhancer to be used for the animal cell expression vector is exemplified by SV40 early gene and late gene, adenovirus major late promoter region, globulin enhancer promoter region, LTR of RNA virus, metallothionein promoter region, $\beta$-actin promoter, etc. The replication origin may be prepared by incorporating the replication origin of SV40 or other virus (e.g. polyoma, adeno, VSV, BPV, etc.) into a vector, or replication mechanism of host cell chromosome may be used. As long as the vector can be inserted in the chromosome of host cells, it is sufficient for use.

The DNA coding for DHFR added with a UK promoter at the upstream, intends to allow the DNA coding for DHFR to act under the control of the UK promoter. Said UK promoter and the DNA coding for DHFR are both known, and the UK promoter is disclosed in Nucl. Acids Res., 13, 2759-2771 (1985), and the DNA coding for DHFR is disclosed in EP-A-117060 and EP-A-265874.

In said plasmid, the unit consisting of a promoter capable of controlling expression in animal cells and a DNA coding for mutant human PUK, and the unit consisting of a UK promoter and a DNA coding for DHFR may be located in the forward direction or reverse direction. Also, the plasmid may have a replication origin at the upstream of the DNA unit coding for mutant human PUK added with, at the upstream thereof, a promoter capable of controlling expression in animal cells, and at the downstream thereof, ribosome binding site, RNA splice site, and poly A addition site or transcription termination sequence.

2. Transformant

The transformant can be obtained by transforming animal cells by the plasmid of 1.

The animal cells to be used in the present invention which are useful as cell strain include VERO, HeLa cells, Chinese hamster ovary (CHO) cell line, W138, BHK, COS-7, MDCK cell line, C127, HKG, human kidney cell line, etc. Specifically, CHO-K1 (Chinese hamster ovary cell: ATCC CCL61), BHK (new-born hamster kidney cell: ATCC CCL10), COS-7 (CV-1 origin, SV40 cells: ATCC CRL1651), VERO (African green monkey kidney cell: ATCC CCL-81), etc. may be mentioned. In particular, they are preferably DHFR gene defective cells.

The transformation of animal cells can be conducted by, for example, calcium phosphate precipitation method, protoplast polyethylene glycol fusion method, Electroporation method, etc.

The amplification of gene by MTX (methotrexate) can be performed by cultivating transformants in a medium containing 10 nM-4 $\mu$M MTX, in which the MTX concentration may be stepwise increased or may be high from the beginning in a single step procedure, and selecting resistant cell lines.

The medium is exemplified by MEM-$\alpha$ containing 1-10% FCS, Dulbecco modification-MEM(D-MEM), etc. The cultivation may be conducted at 10°-37° C. for about 1-200 hr.

3. Production of mutant human PUK

The transformant of 2. is cultivated to allow expression of mutant human PUK by a method known per se.

(4) Purification

Purification of mutant human PUK may be conducted according to the known purification method for mutant human PUK (EP-A-139447). In the present invention, column chromatographys using Chelating Sepharose 6B, anti-UK formyl cellurofine 4B, and Benzamidine-Sepharose 6B were used. Of those, Chelating Sepharose 6B is effective for crude purification, anti-UK formyl cellurofine 4B is effective for high purification, and Benzamidine-Sepharose 6B is useful for removing contaminated active UK.

Analysis of the product thus obtained revealed that mutant and non-mutant PUKs showed no difference in PUK activity, and that the mutant PUK is a single strand proenzyme having a molecular weight of about 50,000–55,000, which could be converted to active type by the plasmin treatment. The affinity of this mutant human PUK for fibrin was compared with that of human kidney cell-derived PUK [J. Biol. Chem., 260, 12377 (1985)], and it was found that the affinity of the mutant human PUK could be significantly enhanced.

In the present invention, it has been found that a replacement of a neutral amino acid in the EGF region of human PUK which is a fibrinolysin with a basic amino acid, or a replacement of an acidic amino acid with a non-acidic amino acid can achieve an improved affinity for fibrin, as well as prolonged half-life in blood.

The present invention is hereinafter more detailedly described by way of examples, to which the present invention is not limited.

The following plasmid, enzyme, kit, technique, etc. are used in the present invention.

(a) Plasmid used pUH7: an expression vector disclosed in EP-A-253241, wherein the entire EGF region ($Asn^{10}$-$Cys^{42}$) has been eliminated from cDNA of PUK.

pSV-$G_1$-preUK: an expression vector for human PUK (EP-A-154272)

pTT06: a DHFR expression vector (see Reference Example 1 to be mentioned later)

The structure of the three plasmids is shown in FIG. 1.

(b) Enzyme, kit

Restriction enzyme, T4DNA polymerase, T4 polynucleotide kinase, bacteria-originated alkaline phosphatase (BAP), sequence kit, ligation kit, and JM109 competent cell were purchased from Takara Shuzo, Japan. For the mutagenesis, used was oligonucleotide-directed mutagenesis system ver. 2 (Amersham).

(c) Recombinant DNA technique

A method according to Maniatis et al. "Molecular Cloning" Cold Spring Harbor, N.Y.: Cold Spring Harbor Laboratory (1982) was used.

EXAMPLE 1

Construction of Amino Acid-Replaced Mutant Human PUK Expression Plasmid

I. Construction of $Lys^{16}$-PUK Expression Plasmid (i) Preparation of synthetic primer Using 381A DNA synthesizer (Applied Biosystem), a single strand DNA was prepared. SD16 is a mutagenesis primer wherein $Gly^{16}$ (GGA) of SD16 has been replaced with $Lys^{16}$ (AAA), and KpnI site has been newly introduced (FIG. 2) (SEQ ID NO: 1 & 2). The synthesized DNA was eluted from a column with 3 ml of 30% aqueous ammonia, 1 ml of which was heated overnight and thereafter purified by oligonucleotide purification column (ABJ) to give 133 μg of SD16.

(ii) Construction of single strand DNA, spTT10

Figure 3A:
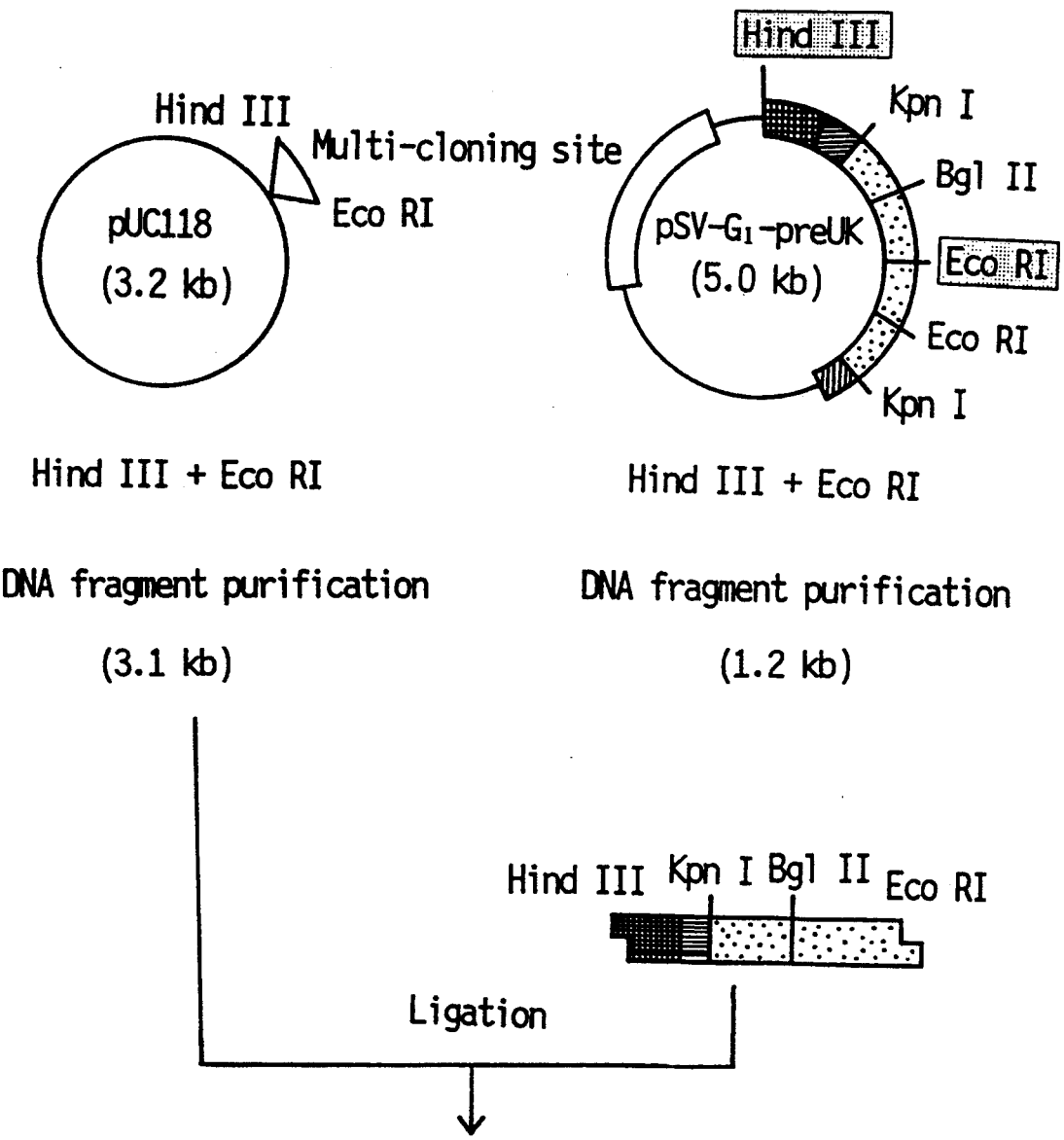
FIG. 3 shows the construction steps of single strand DNA, spTT10.
Figure 3B:
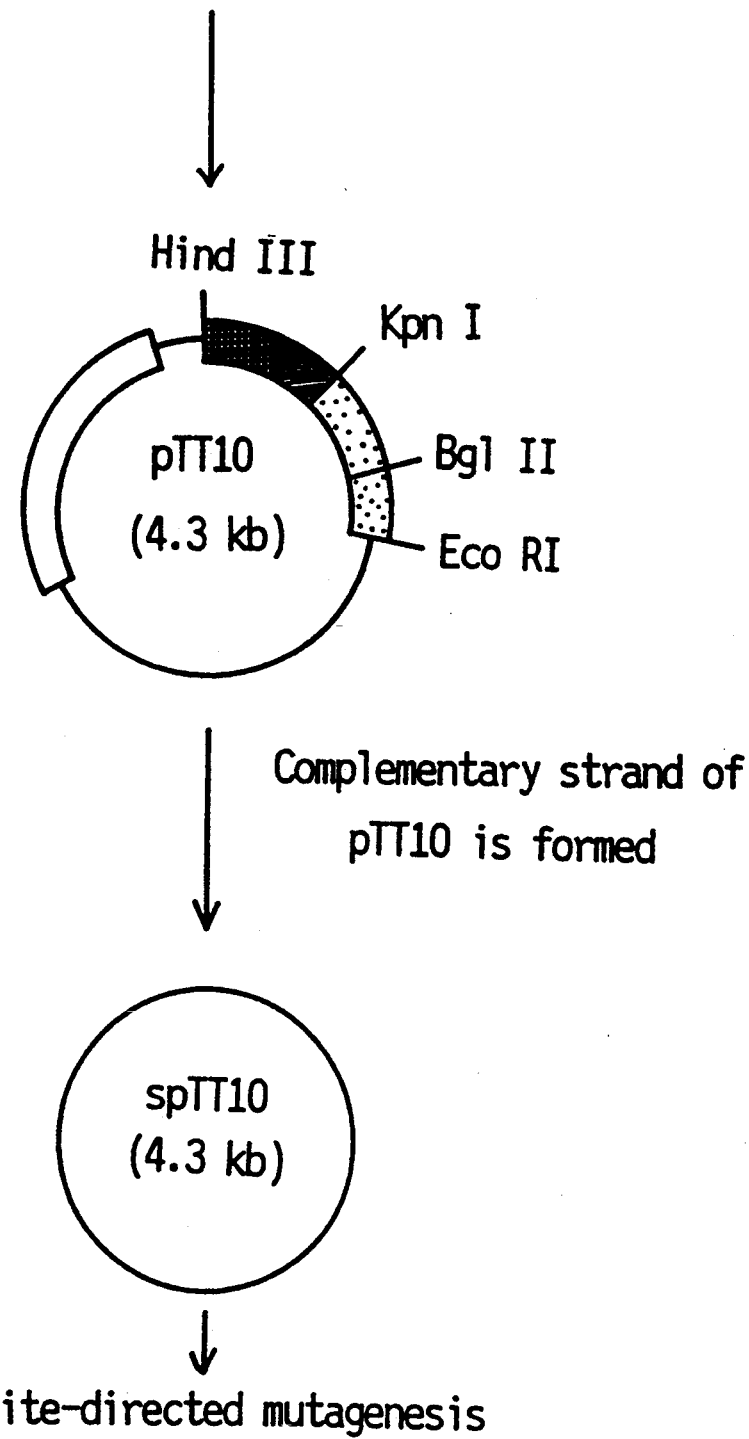

The general flow of the construction steps is shown in FIG. 3. A HindIII-EcoRI fragment (1.2 kb) of pSV-G1-preUK was inserted in between HindIII site and EcoRI site of pUC118 to give pTT10. This DNA fragment had a base sequence coding for the enhancer-promoter and the splicing junction of SV40, and the 653rd base of PUK cDNA, namely, up to $Gly^{162}$ in the kringle domain. Escherichia coli JM109 was transformed with the pTT10 so that it was infected with the herpes virus M13K07 strain. From 240 ml of the culture thereof was prepared a single strand DNA, from which 350 μg of spTT10 was obtained.

(iii) Site-directed mutagenesis

Plasmid pMR326 carrying a DNA coding for $Lys^{16}$-PPA was constructed using primer DNA (SD16) and template DNA (spTT10). Using the pMR326 thus obtained, JM109 was transformed. The sample was subjected to agarose electrophoresis in order to monitor each reaction, and the size of the DNA band was determined.

(iv) Screening of the strain carrying pMR326

Twelve strains were selected at random from the transformants obtained by mutagenesis, and subjected to miniprep for obtaining plasmids. These plasmids were digested with KpnI, electrophoresed in agarose gel, and screened according to the presence or absence of two DNA bands at 4.1 kbp and 220 bp. As a result, it was found that 4 strains out of 12 had the objective plasmid.

(v) Confirmation of mutation by sequencing

So as to confirm that, in the plasmids selected by screening, mutation has occurred at the intended sites, and that other sites have not been mutated during the mutagenesis, the nucleotides between KpnI site and BglII site (430 bp) of pMR326 and the selected plasmids were sequenced by dideoxy method. As a result, it was found that the sequence between base No. 51 in SEQ ID NO: 7 and BglII site was the same.

Figure 4A:
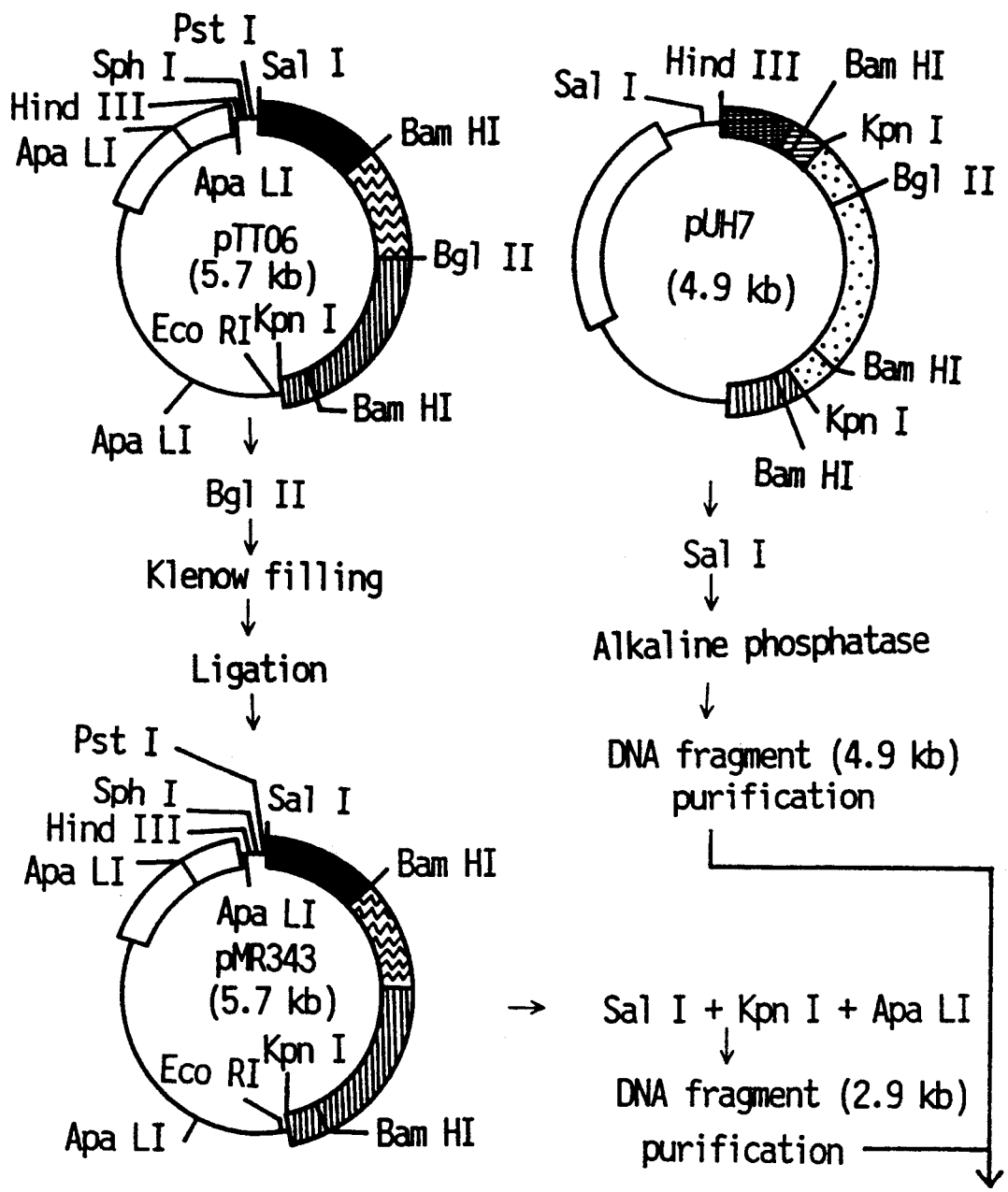
FIG. 4 shows the construction steps of the plasmid having DHFR and $\Delta E_1E_2E_3$-PUK expression units.
Figure 4B:
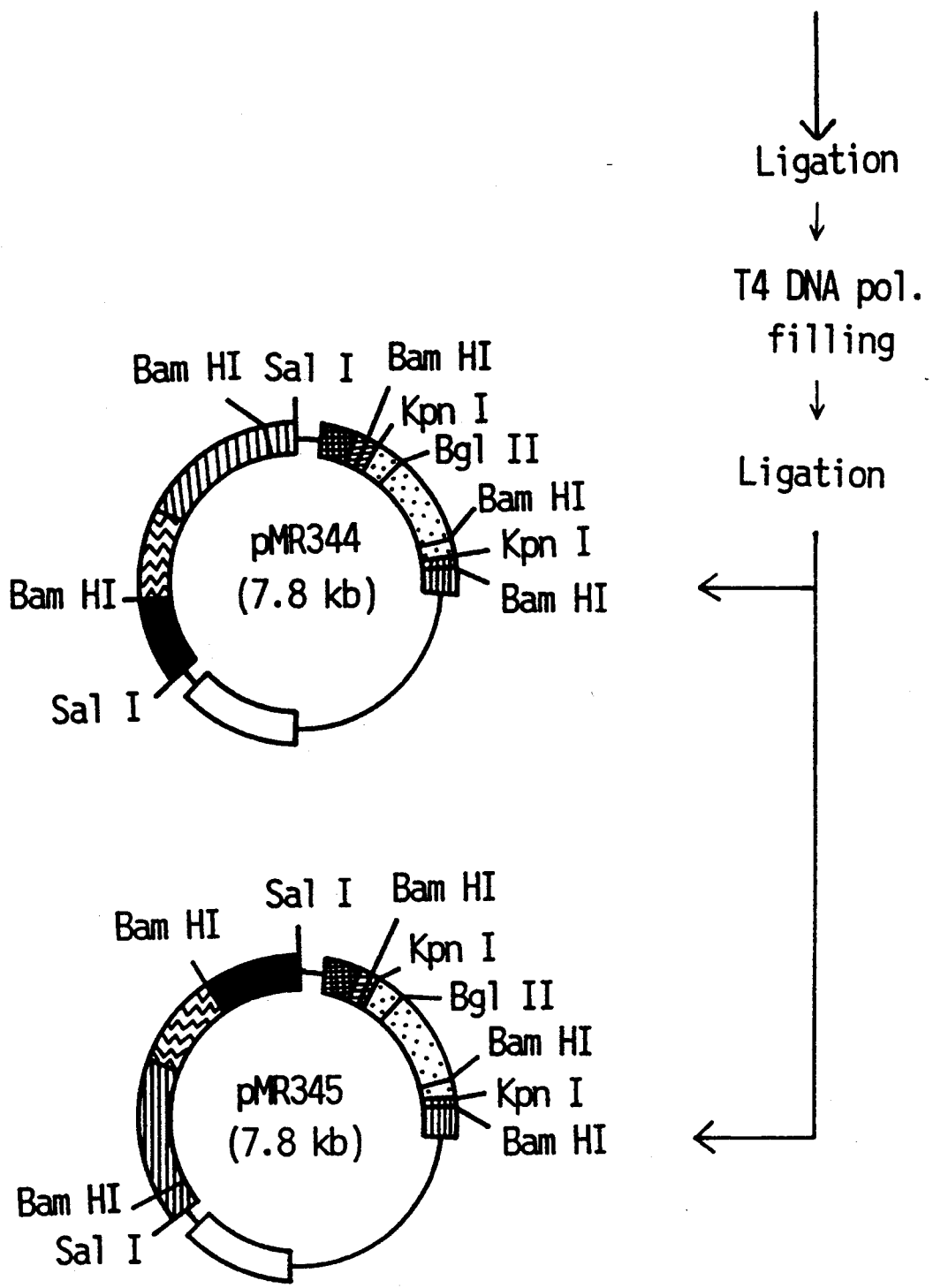

(vi) Construction of plasmid having DHFR expression unit and $\Delta E_1E_2E_3$-PUK expression unit The steps of plasmid construction are shown in FIG. 4. The plasmid having a DHFR gene expression unit, pTT06, was partially digested with BglII, given a blunt end with the Klenow fragment, and subjected to self-ligation to give the plasmid pMR343. By this procedure, the unique site BglII between DHFR cDNA and poly A addition region of SV40 was eliminated. After the pMR343 was digested with three enzymes, SalI, KpnI, and ApaLI, it was subjected to agarose gel electrophoresis, and SalI-KpnI fragment (2.9 kb) obtained which is the DHFR expression unit was purified by DEAE method. This DNA fragment and pUH7 digested with SalI were ligated. Since only SalI site of DHFR expression unit and SalI site on one side of pUH7 were ligated by this reaction, the ends left unligated were given blunt ends with T4DNA polymerase. After the self-ligation, the plasmid was used to transform Escherichia coli JM109. The plasmid war extracted from the colonies obtained, which was then digested with BamHI to confirm the presence of the insert and its direction. Upon electrophoresis, the pMR344 having DHFR expression unit and m-PUK expression unit in the forward direction showed bands at 3.4, 1.6, 1.4, 1.0, and 0.3 kb, and the pMR345 having them in the reverse direction showed bands at 3.1, 1.6, 1.4, 1.3, and 0.3 kb.

(vii) Insertion of mutated DNA fragment into expression vector

Figure 5:
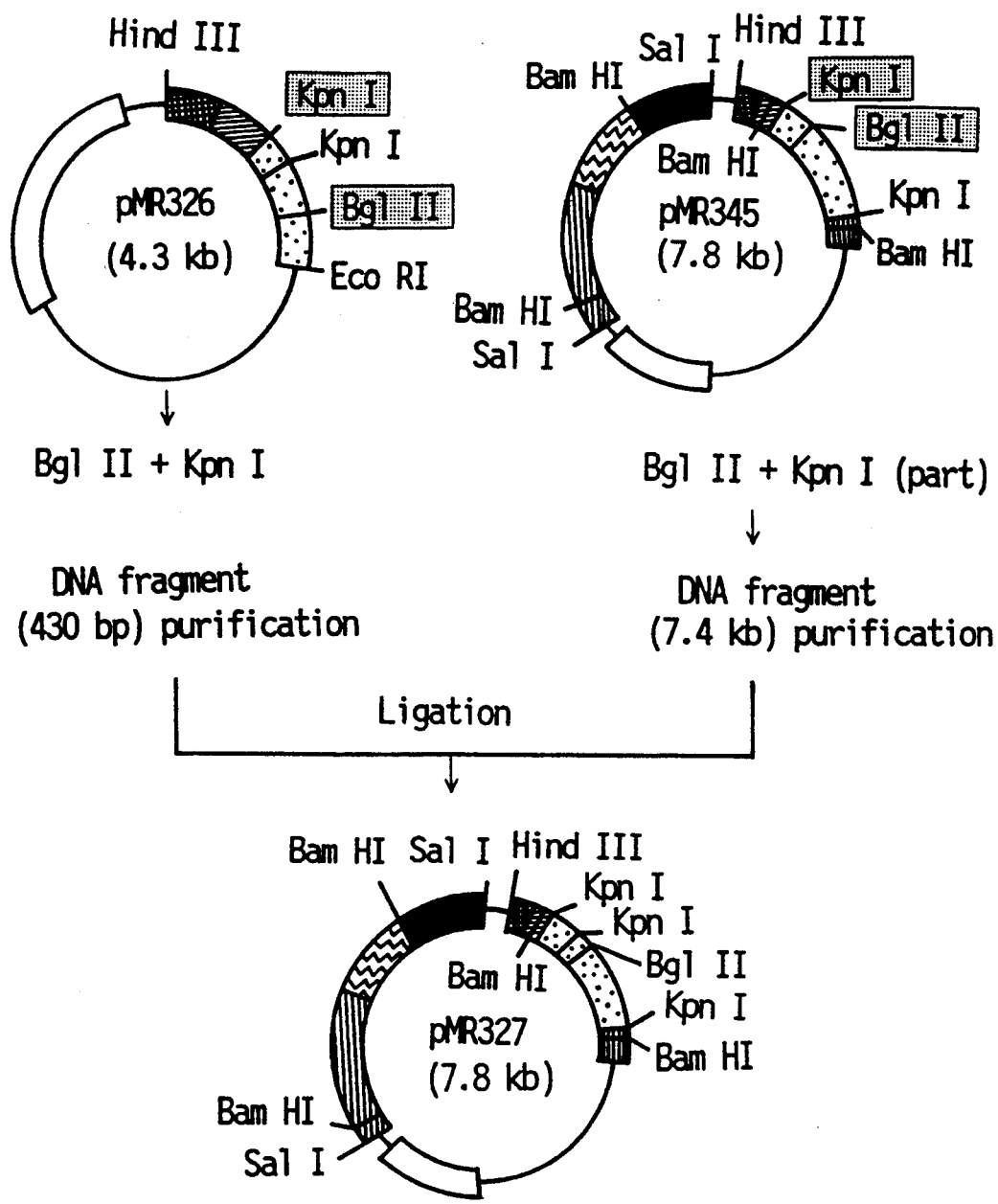
FIG. 5 shows the general construction steps of pMR327.

After the sequence confirmation, KpnI-BglII site (430 bp) of pMR326 was replaced with KpnI-BglII site of pMR345 to give the plasmid pMR327. The general flow of plasmid construction is shown in FIG. 5. This plasmid was prepared in a large amount to give 333 μg of the plasmid which was subjected to transfection.

II. Construction of Lys$^{38}$-PUK expression plasmid (i) Preparation of synthetic primer Using 381A DNA synthesizer (Applied Biosystem), a single strand DNA was prepared. SD13 is a mutagenesis primer wherein Gly$^{38}$ (GGA) has been replaced with Lys$^{38}$ (AAA), and DraI site has been newly introduced (FIG. 6) (SEQ ID NOS: 3, 4 & 8). The synthesized DNA was eluted from a column with 3 ml of 30% aqueous ammonia, 1 ml of which was heated overnight and thereafter purified by oligonucleotide purification column (ABJ).

(ii) Mutagenesis

According to I-(iii) above, pMR316 was constructed from spTT10 and SD13.

(iii) Screening of the strain carrying pMR316

Twelve strains were selected at random from the transformants obtained by mutagenesis, and subjected to miniprep for obtaining plasmid. These plasmids were digested with DraI, electrophoresed in agarose gel, and screened according to the presence or absence of three DNA bands at 2.95, 1.25, and 0.7 kb. As a result, it was found that 4 strains out of 12 had the objective plasmid.

(iv) Confirmation of mutation by sequencing

So as to confirm that, in the plasmids selected by screening, mutation has occurred at the intended sites, and that other sites have not been mutated during the mutagenesis, the nucleotides between KpnI site and BglII (430 bp) of pMR316 and the selected plasmids were sequenced by dideoxy method. As a result, it was found that the sequence between base No. 52 in SEQ ID NO: 7 and BglII was the same.

(v) Insertion of mutated DNA fragment into expression vector

Figure 7:
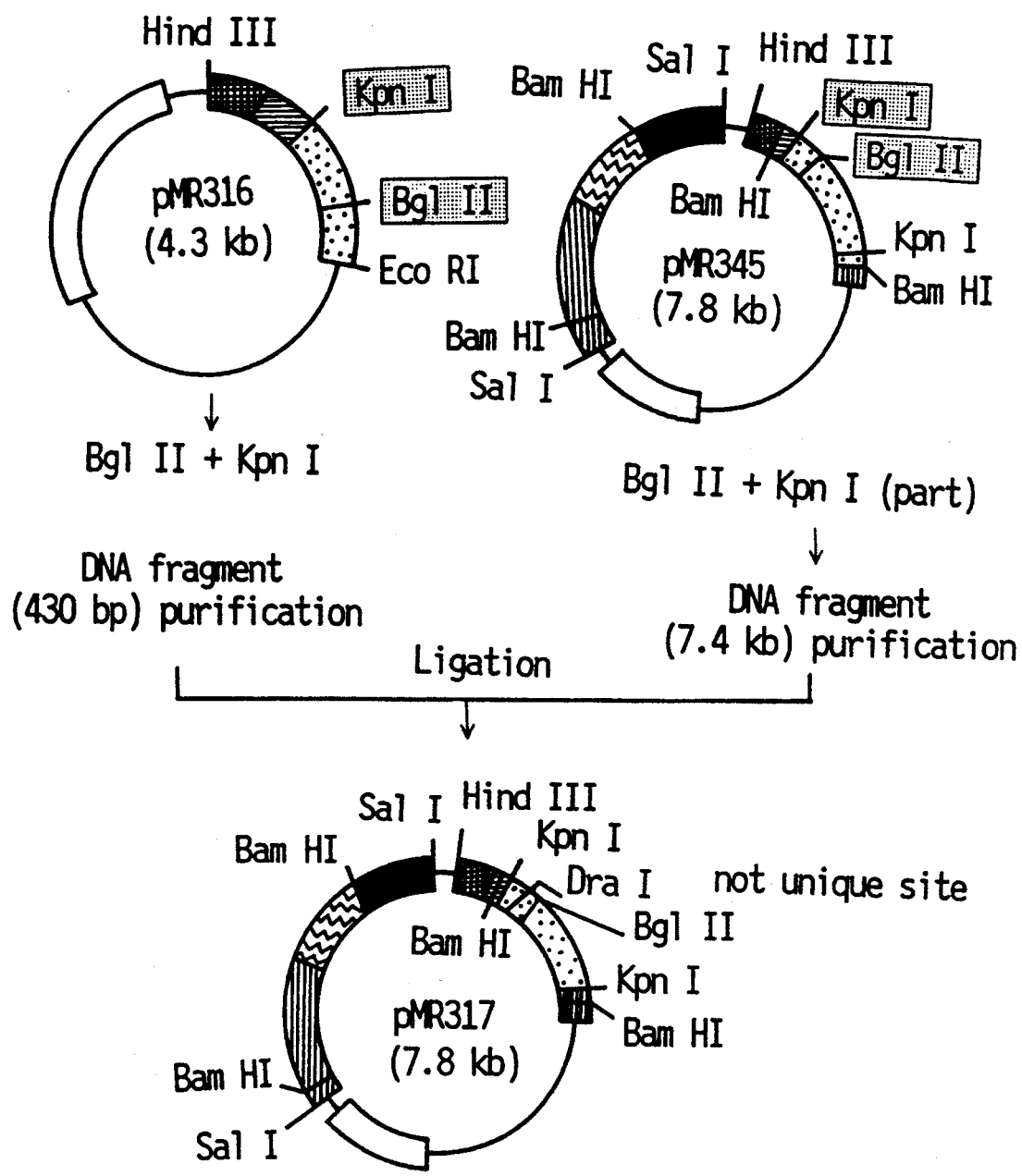
FIG. 7 shows the general construction steps of pMR317.

After the sequence confirmation, KpnI-BglII site (430 bp) of pMR316 was replaced with KpnI-BglII site of pMR345 to give the plasmid pMR317. The general flow of plasmid construction is shown in FIG. 7. This plasmid was prepared in a large amount to give 543 μg of the plasmid which was subjected to transfection.

III. Construction of Asn45-PUK Expression Plasmid (i) Preparation of synthetic primer Using 381A DNA synthesizer (Applied Biosystem), a single strand DNA was prepared. SD30 is a mutagenesis primer wherein Asp$^{45}$ (GAT) has been replaced with Asn$^{45}$ (AAT), and VspI site and Nsp(7524)I site have been newly introduced (FIG. 8) (SEQ ID NO: 5 & 6). The synthesized DNA was eluted from a column with 3 ml of 30% aqueous ammonia, 1 ml of which was heated overnight and thereafter purified by oligonucleotide purification column (ABJ). Obtained were 80 μg of SD30, and 109 μg of SD33.

(ii) Mutagenesis

According to I-(iii) above, pMR347 was constructed from spTT10 and SD30.

(iii) Screening of the strain carrying pMR347

Twelve strains were selected at random from the transformants obtained by mutagenesis, and subjected to miniprep for obtaining plasmid. These plasmids were digested with VspI, electrophoresed in agarose gel, and screened according to the presence or absence of three DNA bands at 2.5, 1.2, and 0.5 kb. As a result, it was found that 2 strains out of 12 had the objective plasmid.

(iv) Confirmation of mutation by sequencing

So as to confirm that, in the plasmids selected by screening, mutation has occurred at the intended sites, and that other sites have not been mutated during the mutagenesis, the nucleotides between KpnI site and BglII site (430 bp) of pMR347 and the selected plasmids were sequenced by dideoxy method. As a result, it was found that the sequence between KpnI site and BglII site was the same except up to the base No. 50 in SEQ ID NO: 7 which could not be sequenced by this method due to its three-dimensional structure.

(v) Insertion of mutated DNA fragment into expression vector

Figure 9A:
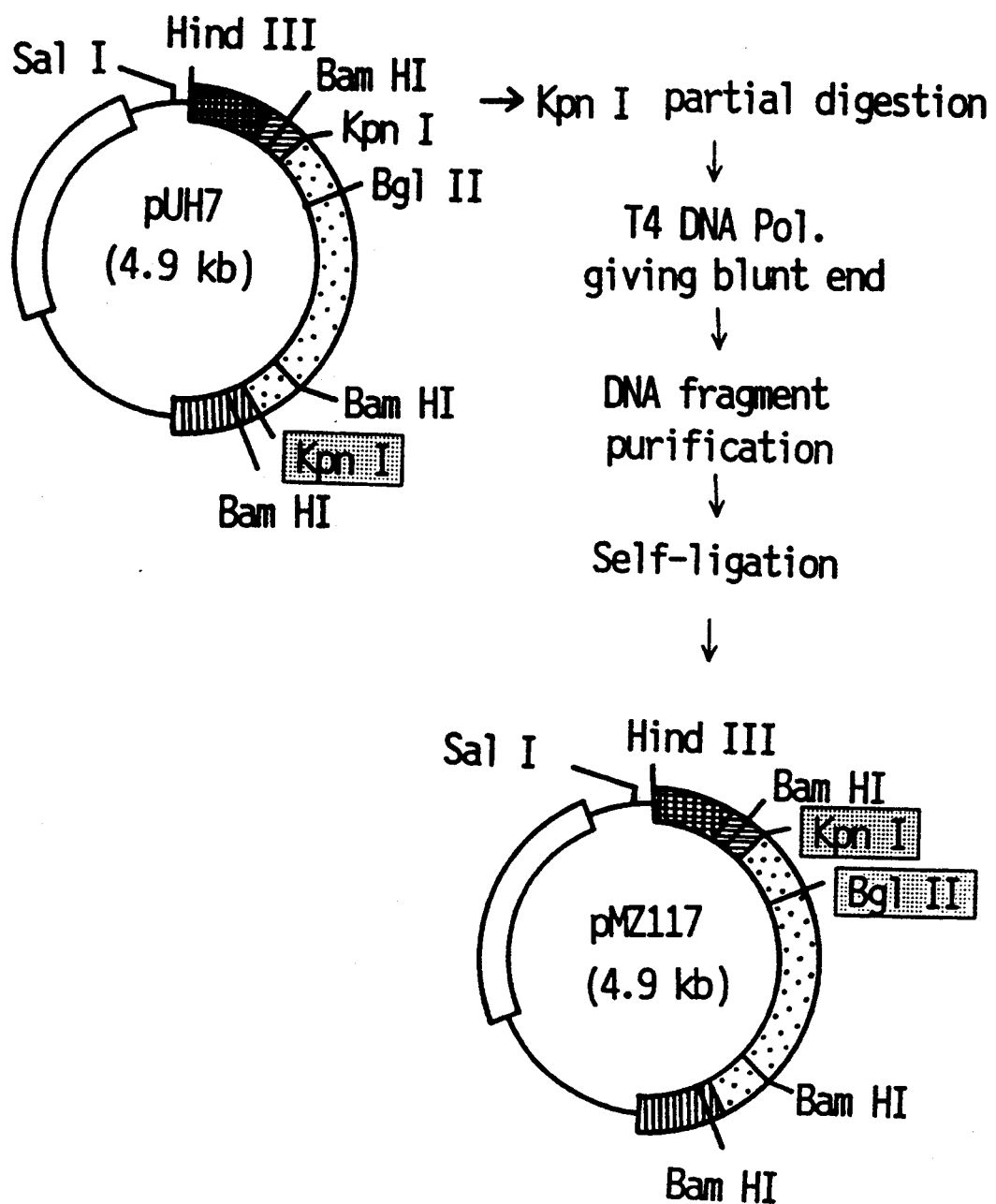
FIG. 9 shows the general construction steps of pMR371.
Figure 9B:
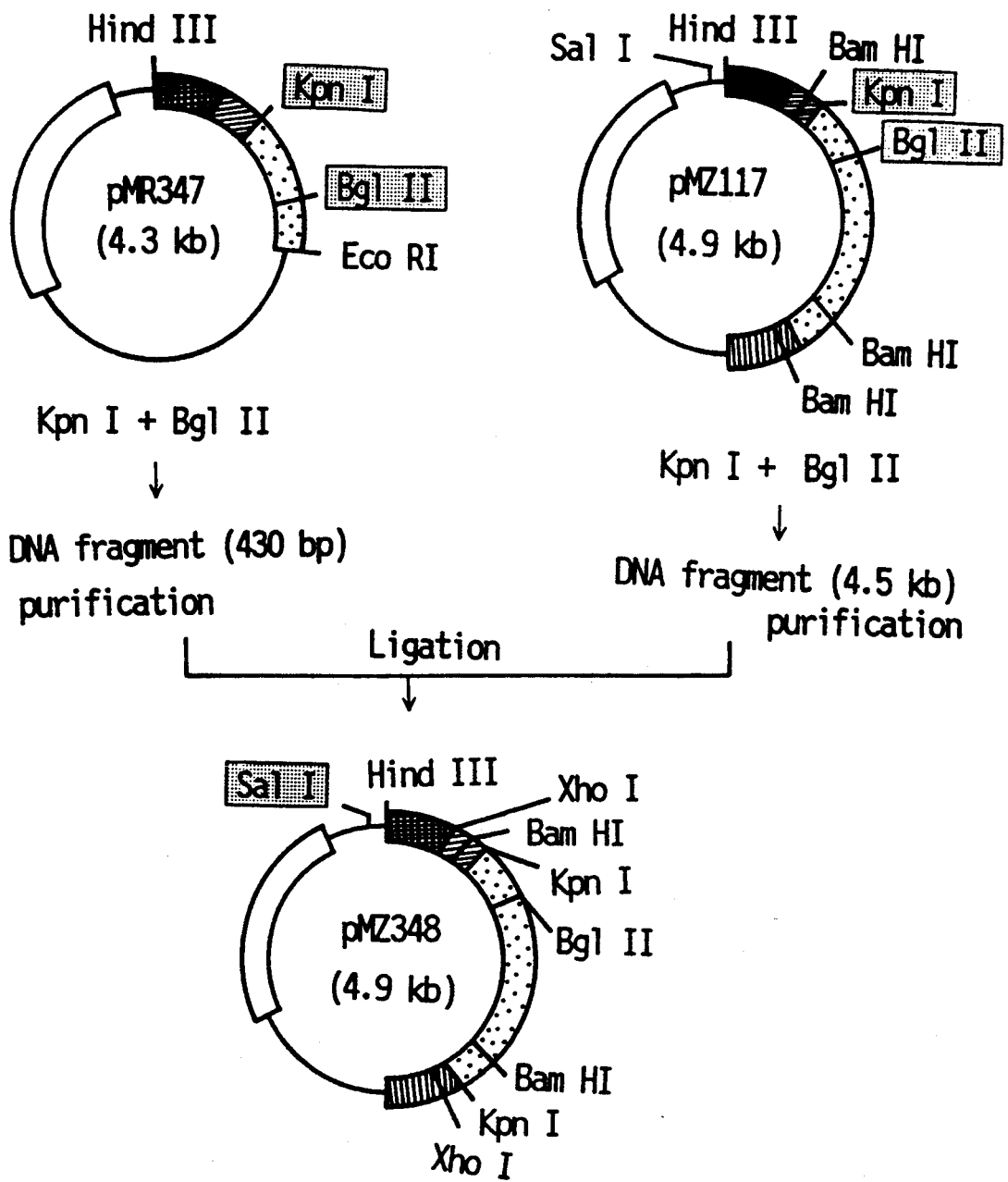
Figure 9C:
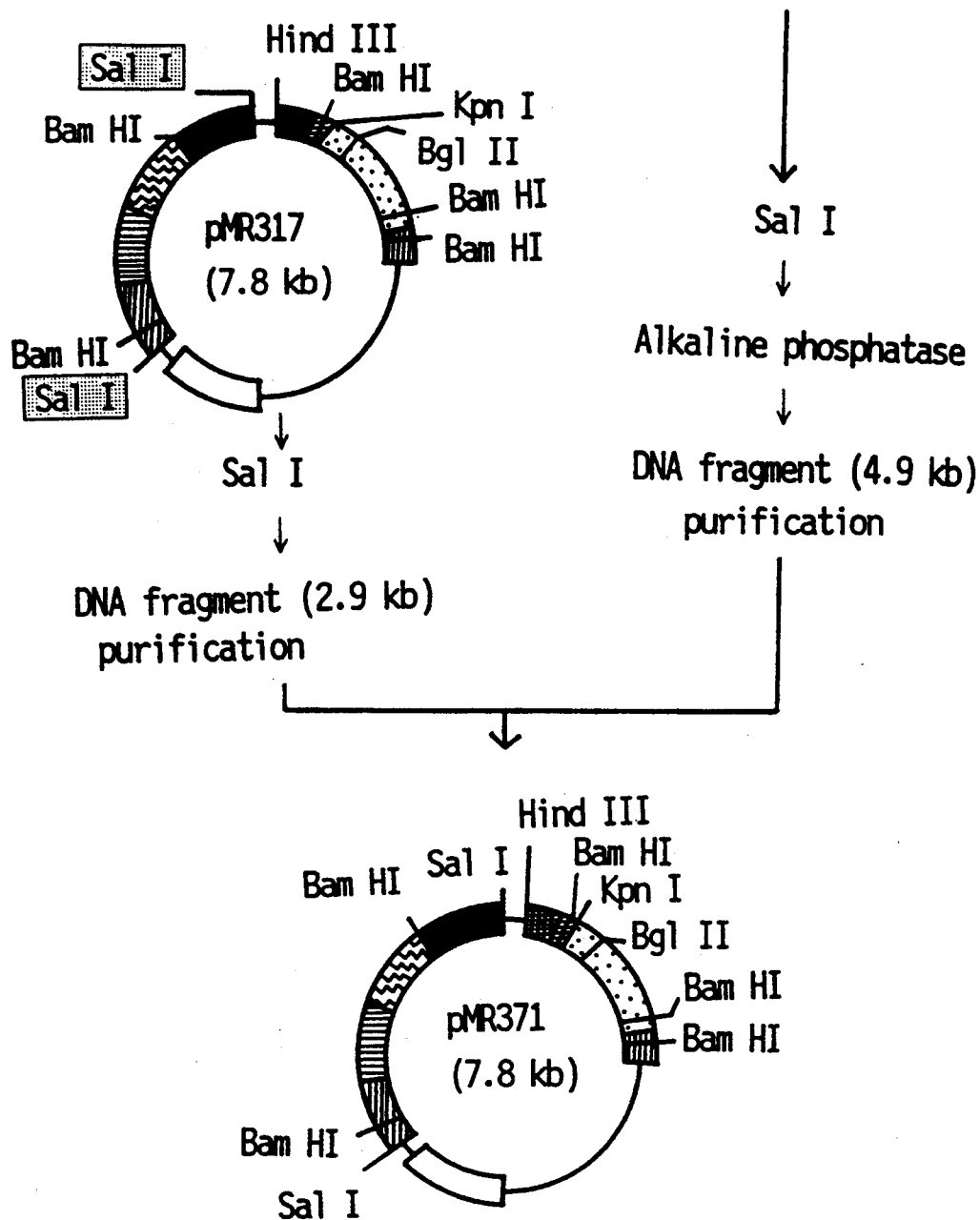
Figure 10:
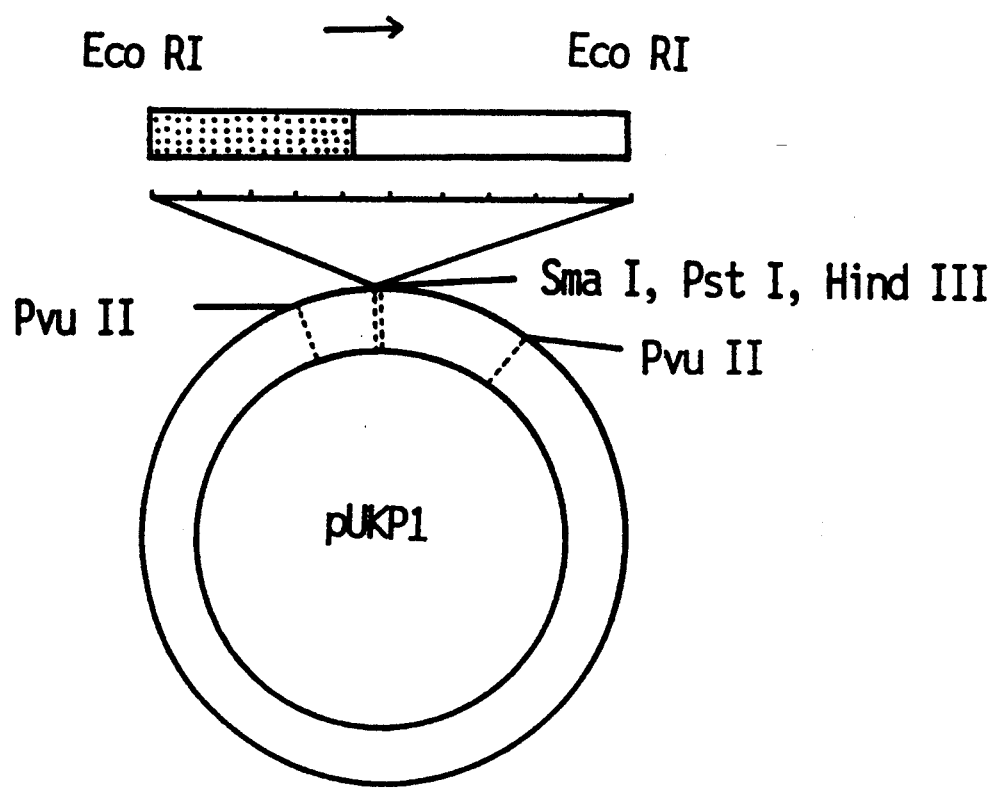
FIG. 10 shows the structure of pUKP1.

After the sequence confirmation, KpnI-BglII (430 bp) of pMR347 was replaced with KpnI-BglII of pMZ117 to give the plasmid pMZ348. The DHFR expression unit (2.9 kb) was cleaved out with SalI from pMR317, and inserted in SalI site of pMZ348. The plasmid obtained was digested with BamHI, based on which the plasmid having DHFR expression unit and m-PUK expression unit in the reverse direction was selected and named pMR371. The general flow of the plasmid construction is shown in FIGS. 9 and 10.

EXAMPLE 2

Production of Amino Acid-Replaced m-PUK (1) Cells

DXB-11 cell: DHFR defective strain derived from CHO-K1 cell, which was prepared and grown according to the method of Proc. Natl. Acad. Sci. (USA), 77, 4216 (1980).

(2) Methotrexate (MTX)

(+)Amethopterin (Sigma) was dissolved in 0.14M NaCl, 0.02 HEPES (Nakarai Tesque, Japan) to give a 2 mM stock solution. When in use, it was added to medium such that the concentration is adjusted as desired.

(3) Medium and serum

MEM-α (with ribonucleoside and deoxyribonucleoside) (Gibco), to be abbreviated as MEM-α (w)

MEM-α (without ribonucleoside and deoxyribonucleoside) (Gibco), to be abbreviated as MEM-α (w/o)

As the serum, used was inactivated fetal bovine serum (FCS) (Mitsubishi Kasei MH01).

(4) DNA introduction and selection of transfectant

DXB-11 cells subcultured in MEM-α (w), 10% FCS were peeled off from a dish by the trypsin treatment (0.25% trypsin, 0.02% EDTA), and suspended in Hanks solution at $10^7$ cell/ml. Plasmid DNA (5 μg) was introduced into 0.5 ml of the suspension, $5 \times 10^6$ cells, by the Electroporation method. The cells were sown on five 10 cm dishes. After incubation in MEM-α (w), 10% FCS for 2 days, the medium was changed to a selective medium MEM-α (w/o), 10% FCS. The medium was changed every 2–3 days. On the 10th day of incubation, colonies formed were moved to a 96-well plate, and the incubation was continued. When the cells in the 96-well plate became nearly confluent, the activity of the plasminogen activator (PA) in each culture supernatant was measured. Several cells which showed high activity were scaled up, and subjected to DNA amplification using MTX.

(5) Amplification of introduced gene with MTX

The amino acid-replaced m-PUK production cells (2 ml) obtained in (4) were inoculated into MEM-α (w/o), 10% FCS, 10 nM MTX medium in a 6-well plate (Falcon, 3046) at $1 \times 10^4$ cell/ml. Although considerable number of cells died after 3 or 4 days of incubation, cells grew while changing medium at every 3 days. Upon 2–4 weeks of incubation, the cells grew sufficient in number, and the medium was changed to the one having an MTX concentration of the next step. In this way, the MTX concentration was increased by 2–4 folds starting from 10 nM. The MTX resistant cells from each concentration were incubated in a 6 cm or 10 cm dish (Falcon, 3803), and the PA activity in the supernatant was determined by fibrin plate method. As the control for the activity measurement, used was Urokinase reference standard (Lot. S-004, The Green Cross Corporation). The increase of m-PUK production by amplification is shown in Table 1.

TABLE 1

MTX concentration and mutant human PUK production (IU/ml)

| | MTX concentration (μM) | | | | | |
|---|---|---|---|---|---|---|
| | 0 | 0.1 | 0.2 | 1 | 2 | 4 |
| $Lys^{16}$-PUK | 6 | 44 | 134 | 643 | 655 | 836 |
| $Lys^{38}$-PUK | 4 | 58 | 110 | 812 | 1520 | — |
| $Asn^{45}$-PUK | 30 | — | 101 | 1327 | — | — |

(6) Incubation of amino acid-replaced m-PUK production cells in a roller bottle

Respective amino acid-replaced m-PUK production cells obtained were scaled up stepwisely, and incubated in a 850 $cm^2$ roller bottle (Falcon, 3027). During the cell growth, MEM-α (w) supplemented with 10% FCS (Mitsubishi Kasei, Lot. MH01) was used, and for harvesting, used was serum-free medium (10.2 g) {RPMI1640 medium as the basal medium [Goding, J. W. (1980), J. Immunol. Methods, 39, 285, JAMA, 199, (1957)] supplemented with insulin (1 mg), BP (beef-derived peptone, 5 g), transferrin (10 mg), HSA (human serum albumin, 1 g), hypoxanthine (13 mg), thymidine (4 mg), α-tocopherol (0.13 mg), and selenium (4 μg)} added with 10 KIU/ml aprotinin (Sigma). One 10 cm dish of the cells were subcultured in a 175 $cm^2$ roller bottle, and then scaled up to a 850 $cm^2$ roller bottle. When the cells became confluent in a roller bottle, the medium for growth was changed to the medium for harvesting, and the incubation was continued. The culture supernatant was harvested every 2 or 3 days according to m-PUK production of the cell. Four or 5 times of harvesting without subculture was possible, and further harvesting was conducted after subculture where necessary. The PA activity in the culture supernatant was determined by peptide MCA method.

EXAMPLE 3

Purification of Amino Acid-Replaced m-PUK

The culture supernatant was passed through a 5 μm filter, and chromatographed on a Zn-chelating Sepharose column. Adsorption and washing were conducted with 1M NaCl, 20 mM Tris-Cl, pH 7.5, 10 KIU/ml aprotinin, and elution was conducted with 1M NaCl, 20 mM Tris-Cl, 50 mM Imidazole, pH 7.5, 10 KIU/ml aprotinin.

The eluted fraction obtained was treated by anti-UK antibody formyl cellulofine column chromatography. Adsorption and washing were conducted with 0.5M NaCl, 0.1M Na-PO$_4$, pH 6.5, and elution was conducted with 0.5M NaCl, 0.2M Glycine-Cl, pH 2.5.

The eluted fraction obtained was adjusted to pH 6.3 with 2M Tris solution, and dialyzed against 0.5M NaCl, 0.1M Na-PO$_4$, pH 6.2. The dialyzed fraction was subjected to Benzamidine Sepharose column chromatography. Adsorption and washing were conducted with 0.5M NaCl, 0.1M Na-PO$_4$, pH 6.2, and unadsorbed fractions were collected. The results are summarized in Table 2.

TABLE 2

Production of mutant human PUK

| | Recovery (%) | | Specific activity | pro content |
|---|---|---|---|---|
| | PUK activity | $A_{280}$ | (U/$A_{280}$) | (%) |
| $Lys^{16}$-PUK | 58 | 0.25 | 102900 | 99.8 |
| $Lys^{38}$-PUK | 62 | 0.17 | 80920 | 99.9 |
| $Asn^{45}$-PUK | 66 | 0.04 | 77850 | 100 |

EXAMPLE 4

Affinity for Fibrin (i) Preparation of fibrin-Celite column

The method of Husain et al. was somewhat modified.

Buffer A: 50 mM sodium phosphate (pH 7.4), 1 mM EDTA, 100 mM NaCl

Buffer B: 50 mM sodium phosphate (pH 7.4), 1 mM EDTA, 100 mM NaCl, 0.2M Arginine Buffer C: 50 mM sodium phosphate (pH 7.4), 1 mM EDTA, 100 mM NaCl, 0.02% $NaN_3$ Celite (Hyflo Super-Cel, Nakarai Kagaku, Japan, 10 g) was suspended in 1 l of distilled water, and left standing for 1 hour. After the supernatant was removed, it was suspended in distilled water again. Celite was received with a Buchner funnel, and washed with Buffer A. Celite was suspended in 50 ml of Buffer A, and 2% plasminogen-free fibrinogen (Seikagaku Kogyo, Japan) in 50 ml of Buffer A was added thereto. The mixture was kept at 30° C., and 100 units/ml thrombin in 0.15M NaCl (2 ml) was added by one drop over 1 minute while stirring, followed by 15 minutes' stirring at 30° C. Immediately thereafter, the mixture was suctioned on a glass filter, and washed with 100 ml of Buffer A. Said procedure was repeated with Buffer A or Buffer B, followed by suction on a glass filter, after which it was suspended in 100 ml of Buffer C. About 5 ml of fibrin-Celite in a settled volume was packed in a column, and the rest was stored at 4° C. Upon equilibration with Buffer A (flow rate 10 ml/hr), it was subjected to the experiment.

(ii) Determination of fibrin bound to Celite

1N NaOH (5 ml) was added to 1 ml of fibrin-Celite (settled volume), and the mixture was heated at 90° C. for 15 minutes. After cooling at room temperature, the absorbance of the supernatant at 280 nm was measured. The fibrin amount in the sample was calculated from the calibration curve obtained by treating a fibrin solution having a known concentration in the same manner as in the above.

(iii) Preparation of sample

Immediately before use, n-PUK (Lot No. T-012), $\Delta E_1 E_2 E_3$-PUK (Lot No. C-006), and three kinds of m-PUKs were diluted with Buffer A' [50 mM sodium phosphate (pH 7.4), 1 mM EDTA, 100 mM NaCl, 0.1% BSA] such that the concentration became 5000 IU/ml.

(iv) Adsorption on fibrin-Celite

Three cycles of measurement was performed for each PUK by batch process. The outline of the steps is given below.

(a) Equilibration with Buffer A'

Fibrin-Celite buffer was dispensed into a 15 ml centrifugation vessel (Coning, #25311) such that the column volume after centrifugation became 1 ml, and centrifuged in a table centrifuge at 1300 rpm for 30 seconds, followed by removal of supernatant. Buffer A' (10 ml) was added thereto, and the mixture was rotated in a rotating machine (Taiyo Kagaku Kogyo, Japan, Rotator II) at 30 rpm (rotation scale 5) for 5 minutes, after which it was centrifuged in a table centrifuge at 1300 rpm for 30 seconds, and the supernatant was removed.

(b) Washing with Buffer A'

A PUK sample (500 μl) adjusted to 5000 IU/ml with Buffer A' was added, and the mixture was stirred for 10 minutes. Immediately thereafter, 10 ml of Buffer A' was added, followed by rotation in a rotating machine at 30 rpm for 5 minutes, after which it was centrifuged in a table centrifuge at 1300 rpm for 30 seconds. The supernatant was removed, and stored for use in activity measurement (pass fraction).

(c) Elution with Buffer B'

Buffer B' (Buffer A' containing 0.2M arginine, 10 ml) was added, and the mixture was rotated in a rotating machine at 30 rpm for 5 minutes, after which it was centrifuged in a table centrifuge at 1300 rpm for 30 seconds. The supernatant was removed, and stored for use in activity measurement (eluted fraction). The PA activity in each supernatant (10 ml) was measured by fibrin plate method.

(v) Calculation of adsorption on fibrin-Celite

The pass fraction refers to the supernatant obtained by washing with Buffer A', and the eluted fraction refers to the supernatant obtained by elution with Buffer B'. The percent adsorption is calculated by the following formula.

$$\% \text{ Adsorption} = \frac{\text{Total UK activity of eluted fraction}}{\text{Total UK activity of pass fraction} + \text{Total UK activity of eluted fraction}} \times 100$$

TABLE 3

| Adsorption of mutant human PUK on fibrin | |
|---|---|
| | Adsorption (%) |
| Lys$^{16}$-PUK | 93.64 ± 1.94[1] |
| Lys$^{38}$-PUK | 97.63 ± 0.90[2] |
| Asn$^{45}$-PUK | 93.05 ± 1.38[1] |
| n-PUK | 81.45 ± 4.88 |
| ΔE$_1$E$_2$E$_3$-PUK | 6.22 ± 2.71 |

[1] $p < 0.05$, significantly higher than n-PUK
[2] $p < 0.01$, significantly higher than n-PUK

EXAMPLE 5

Properties of Mutant Human PUK (i) Specific activity

The specific activity was the same for the three kinds of mutant human PUKs (Lys$^{16}$-PUK, Lys$^{38}$-PUK, Asn$^{45}$-PUK) and was 150,000 IU/mg protein upon plasmin treatment.

(ii) Molecular weight

According to the method of Laemmli [Nature, 227, p680 (1970)], SDS-PAGE (SDS-polyacrylamide gel electrophoresis) was conducted under the conditions mentioned below. Various mutant human PUKs (180–350 IU) were boiled at 100° C. for 10 minutes in a reduction solution of 2% 2-mercaptoethanol, 2% SDS, 10% glycerin, and 50 mM Tris-HCl (pH 6.8), and layered on 10–20% gradient gel (Daiichi Kagaku Yakuhin, Japan), followed by 2 hours' electrophoresis under a constant current of 30 mA. As the molecular marker, used was low-molecular-weight marker (phosphorylase b 94000, bovine serum albumin 67000, ovalbumin 43000, carbonic anhydrase 30000, trypsin inhibitor 20100, α-lactalbumin 14400, Pharmacia). The band on the gel was stained with Coomassie Brilliant Blue R-250. As a result, the same band was observed at about 54000 for all three mutant human PUKs. No band transfer was observed under the reducing or nonreducing conditions for the three mutant human PUKs, which result indicated that they have a single strand molecular structure.

(iii) Enzyme kinetic examination

Materials and method (a) Reagents

Glt-Gly-Arg-MCA (hereinafter abbreviated as MCA) and 7-amino-4-methyl-coumarin (hereinafter abbreviated as AMC) were purchased from Peptide Laboratories. UK standard, and Plasmin were obtained from The Green Cross Corporation.

(b) Determination of initial reaction speed

A mutant human PUK (30 IU/ml, 50 p μl) and plasmin (0.2 CU/ml, 50 μl) were mixed, and incubated at 37° C. for 10 minutes. A 2.0, 0.4, 0.25, 0.2, or 0.15 mM MCA solution (50 μl) heated to 37° C. beforehand was added thereto, followed by 3 minutes' incubation at 37° C. A 40% acetic acid solution (50 μl) was added to terminate the reaction, and the fluorescence intensity was measured. The fluorescence intensity of AMC (0.2, 5, 10, 20 μM) was measured, and calibration curve was drawn, based on which the concentrations of the AMC produced by enzyme reaction were calculated.

(c) Calculation of $K_m$ and $K_{cat}$ values

In accord with the Lineweaver-Burk plot method [Segei, I. H. (1976) Biochemical Calculations, 2nd ed. John Wiley & Sons, Inc., New York], $K_m$ value and $K_{cat}$ value were obtained. Since 1 IU of UK corresponds to $1.33 \times 10^{-7}$ μmole, $K_{cat}$ value was calculated by the following formula.

$$K_{cat} = \frac{V_{max}}{1.33 \times 10^{-7}} \text{ (min}^{-1})$$

The enzyme kinetic constant of each mutant human PUK is shown in Table 4.

TABLE 4

| Enzyme kinetic constant of mutant human PUK | | | |
|---|---|---|---|
| | $K_m$ (μM) | $K_{cat}$ × $10^2$ (min$^{-1}$) | $K_{cat}/K_m$ |
| n-PUK | 310 ± 87 | 43 ± 10 | 14 ± 2 |
| Lys$^{16}$-PUK | 316 ± 159 | 46 ± 10 | 17 ± 5 |
| Lys$^{38}$-PUK | 260 ± 104 | 36 ± 1 | 17 ± 7 |
| Asn$^{45}$-PUK | 290 ± 59 | 44 ± 4 | 16 ± 3 |

In the Table, the figures show mean value±S. D. (n=3)

As shown in Table 4, there was no marked difference among enzyme-kinetic constants of mutant human PUKs.

(iv) Half-life in blood

Experiment method (a) Administered animal

Male Wister rat (6 weeks old) was used.

(b) $^{125}$I-PUK preparation

Each drug was labeled with $^{125}$I by lactroperoxidase enzymobeads (BIO-RAD) method. The radiochemical specific activity of the $^{125}$I-PUK obtained was calculated from the protein content and radioactivity obtained from absorbance at 280 nm. The specific activity of each drug was 6000-10000 cpm/IU.

(c) Dose and administration route

The solution to be administered was adjusted to $2\times10^4$ IU/ml (human albumin concentration: 5%) with a non-labeled drug, and administered via the tail vein at a dose of 1 ml/kg.

(d) Blood sampling

The test animal was anesthetized with 35 mg/kg of Ketaral (Sankyo, Japan), i.m., and 1.5 g/kg of Urethane (Nakarai Kagaku, Japan), i.m., and fixed at the dorsal position. An Atom venous catheter (3Fr) filled with 3.8% aqueous sodium citrate [Citrate, The Green Cross Corporation] was inserted from left carotid. At 1, 2, 3, 5, 7, 10, 15, and 20 minutes after the drug administration, blood was taken with a JMS 1 ml disposable syringe containing 30 μl Citrate to the scale of 330 μl (300 μl blood). One hundred μl from the plasma obtained by 10 minutes' centrifugation at 3000 rpm was rapidly freezed on dry ice, and the radiation of the plasma was measured by a γ-counter.

(e) Analysis of the concentration change in plasma

The radioactivity in the plasma was calculated in % of dose, and half-life in blood was calculated using a marketed software.

(f) Experiment results

The half-life in blood is as shown in Table 5. The half-life in blood as seen from the radioactivity of the mutant human PUK newly screened this time was prolonged 1.2-1.4 times that of n-PUK, and showed a significant improvement.

TABLE 5

| half-life of mutant human PUK in blood | |
|---|---|
| | Half life time (min.) |
| n-PUK | 2.3 ± 0.2 |
| Lys$^{16}$-PUK | 2.9 ± 0.5 |
| Lys$^{38}$-PUK | 2.7 ± 0.2 |
| Asn$^{45}$-PUK | 3.4 ± 0.3 |

The values are mean value ±S.D. (n=3)

(v) Thrombolytic activity

The experiment was conducted using a male Wister rat model having pulmonary embolus.

(a) Improvement in the preparation of $^{125}$I-fibrin suspension ($^{125}$I-FS)

To 40 ml of citrated plasma of rat was added about 60 μCi of $^{125}$I-fibrinogen. After mixing, the mixture was dispensed by 2 ml. Thereto were added CaCl$_2$ and thrombin in such a manner that the final concentration became 25 mM and 10 U, respectively, and the mixture was incubated at 37° C. for 30 minutes to cause clotting. The clot formed was washed with physiological saline, and pulverized in a mortar cooled with liquid nitrogen. Physiological saline (5 ml) was added thereto to give $^{125}$I-FS.

(b) Preparation of a rat model with pulmonary embolus and administration of the test drug A rat weighing 216-263 g was anesthetized by subcutaneous administration of 1.25 g/kg Urethane, and 2% NaI solution (100 μl) was injected via the tail vein. Thereafter, 1 ml of $^{125}$I-FS (radioactivity measured in advance) was administered via the tail vein to form pulmonary embolus. At 5 minutes after the $^{125}$I-FS administration, the test drug (100,000 IU/kg) was bolus administered via the tail vein, in which the dose was always adjusted to 1.5 ml with vehicle. At 60 minutes after the $^{125}$I-FS administration, the animal was slaughtered. The radioactivity of residual $^{125}$I-fibrin in lung was measured, based on which percent thrombolysis was estimated. The percent thrombolysis was calculated from the following formula.

% Thrombolysis=100−(residual $^{125}$I-FS in lung$^{1)}$/residual $^{125}$I-FS in lung at 5 *minutes after administration*$^{2)}$)×100

$^{1)}$ residual radioactivity in lung at the termination of the experiment (%)
$^{2)}$ residual radioactivity in lung at 5 minutes after the $^{125}$I-FS administration when rat was slaughtered (%)

The results are shown in Table 6.

TABLE 6

| Thrombolytic ability of mutant human PUK | |
|---|---|
| | Percent thrombolysis (%) |
| Lys$^{16}$-PUK | 42.0 ± 7.7 |
| Lys$^{38}$-PUK | 48.3 ± 2.2 |
| Asn$^{45}$-PUK | 39.6 ± 5.6 |
| n-PUK | 33.8 ± 2.7 |
| vehicle | 14.3 ± 1.6 |

The values are mean value ±S.D. (n=5)

REFERENCE EXAMPLE 1

Construction of pTT06 (Construction of plasmid inserted with a DNA coding for DHFR and added with a UK promoter at the upstream)

(i) Construction of pUKP-I: Preparation of DNA coding for UK promoter (a) Preparation of probe Plasmid pUK4 (EP-B-154272) containing a part of human UK cDNA was digested with PstI. After electrophoresis in 1% agarose gel, about 400 bp fragment was recovered by electroelution. This DNA fragment (0.4 μg) was labeled with [α-$^{32}$P]dCTP (Amersham, PB10205) using multi-prime.

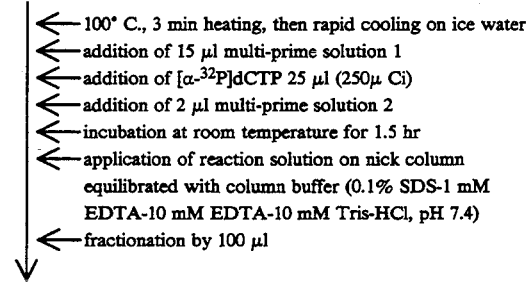

NDA fragment 0.4 μg (8 μl)
← 100° C., 3 min heating, then rapid cooling on ice water
← addition of 15 μl multi-prime solution 1
← addition of [α-$^{32}$P]dCTP 25 μl (250μ Ci)
← addition of 2 μl multi-prime solution 2
← incubation at room temperature for 1.5 hr
← application of reaction solution on nick column equilibrated with column buffer (0.1% SDS-1 mM EDTA-10 mM EDTA-10 mM Tris-HCl, pH 7.4)
← fractionation by 100 μl The objective fractions were collected, and Cerenkov count was determined to be $9.69\times10^7$ cpm. Yield of the label was 41%, and radioactivity of the label was $2.4\times10^8$ cpm/μg.

(b) Southern hybridization of HKG cell DNA

According to the report by Riccio et al. [Nucl. Acids Res., 13, 2759-2771 (1985)], human urokinase promoter region can be obtained as 5.8 kb EcoRI fragment and 12 kb BamHI fragment of human chromosome DNA. HKG cell high-molecular-weight DNA was digested with EcoRI and BamHI, and 10 μg each was subjected to electrophoresis in 0.8% agarose gel. Using the probe prepared in (a) above, Southern hybridization was performed to confirm the objective fragment. As a result, signals were detected at the site corresponding to each size.

(c) Preparation of 5.8 kb EcoRI fragment

HKG cell high-molecular-weight DNA (200 μg) was digested overnight at 37° C. with 1000 units EcoRI. After electrophoresis in 0.8% agarose gel (Takara Shuzo, Japan, HE-12 electrophoresis apparatus), the DNA was stained with ethidium bromide, and electrophoresed as a marker. A gel (gel 2) was cleaved out at 2 mm width about the 5.8 kb site estimated from λ-DNA digested with HindIII, and an upper gel (gel 1) and a lower gel (gel 3) were also cleaved out at 3 mm width. By electroelution, DNA fragments were extracted. A portion of the DNAs extracted was electrophoresed in 0.8% agarose gel, and the presence of the objective DNA fragment was confirmed by Southern hybridization. It was speculated that the objective urokinase promoter region existed in the DNA fragment extracted from gel 2.

(d) Construction of DNA library and screening

A DNA library was constructed from the DNA extracted in (c) above, using the phage vector $\lambda_{gt}10$. The total $6.5 \times 10^5$ recombinant phages were subjected to primary screening by plaque hybridization, thereby obtained were 28 positive clones. These clones were further subjected to secondary screening by plaque hybridization to give 5 positive clones. DNAs were extracted from recombinant phages of the positive clones by simple extraction method, which were then digested with EcoRI, electrophoresed in 1% agarose gel, and subjected to Southern hybridization. As a result, two kinds of recombinant phages were determined to be positive. Clones 1, 4, and 5 were derived from the same clone, and regarded as one kind. Clone 15 was derived from another clone.

(e) Subcloning of 5.8 kb EcoRI fragment

Phage DNAs were prepared by simple extraction method from the clones determined to be positive by Southern hybridization, and digested with EcoRI. The DNAs were extracted with phenolchloroform, and the aqueous layer was further extracted with chloroform and precipitated with ethanol. Plasmid pUC9 (Pharmacia) was digested with EcoRI, and treated with alkaline phosphatase. A portion (1 μg) thereof and the above-mentioned phage DNA digested with EcoRI were ligated, and E. coli HB101 was transformed. Plasmid DNAs were extracted from some transformant cells by simple extraction method, which were then digested with EcoRI, and electrophoresed in 1% agarose gel. As a result, it was found that some subclones possessed the DNA fragment corresponding to 5.8 kb. These clones 1 and 4 were digested with various restriction enzymes, and electrophoresed in 1% agarose gel. While cleaving method was different for clone 1 and clone 4, it was speculated that 5.8 kb fragments were inserted in the opposite directions, since some common fragments could be observed. The plasmids obtained were named pUKP1 (see FIG. 10) and pUKP2.

(f) Restriction enzyme treatment of pUKP1

Based on the restriction enzyme cleavage site map speculated from the base sequence of human urokinase gene reported by Riccio et al (mentioned earlier), whether or not the enzyme fragment inferred from the map can be obtained was confirmed. E. coli HB101 possessing pUKP1 was incubated overnight in super broth (100 ml) containing 40 μg/ml ampicillin, and a plasmid DNA was prepared by miniprep method. This DNA was treated with various restriction enzymes. All the putative restriction enzyme fragments were detected from the plasmid, thereby it was confirmed that the DNA fragment coding for the objective human urokinase promoter site was cloned.

(g) Confirmation of partial base sequence of pUKP1

A portion of the base sequence of the plasmid DNA prepared in the preceding section was investigated by dideoxy method, and found to be identical with what was reported by Riccio et al (mentioned earlier).

Figure 11A:
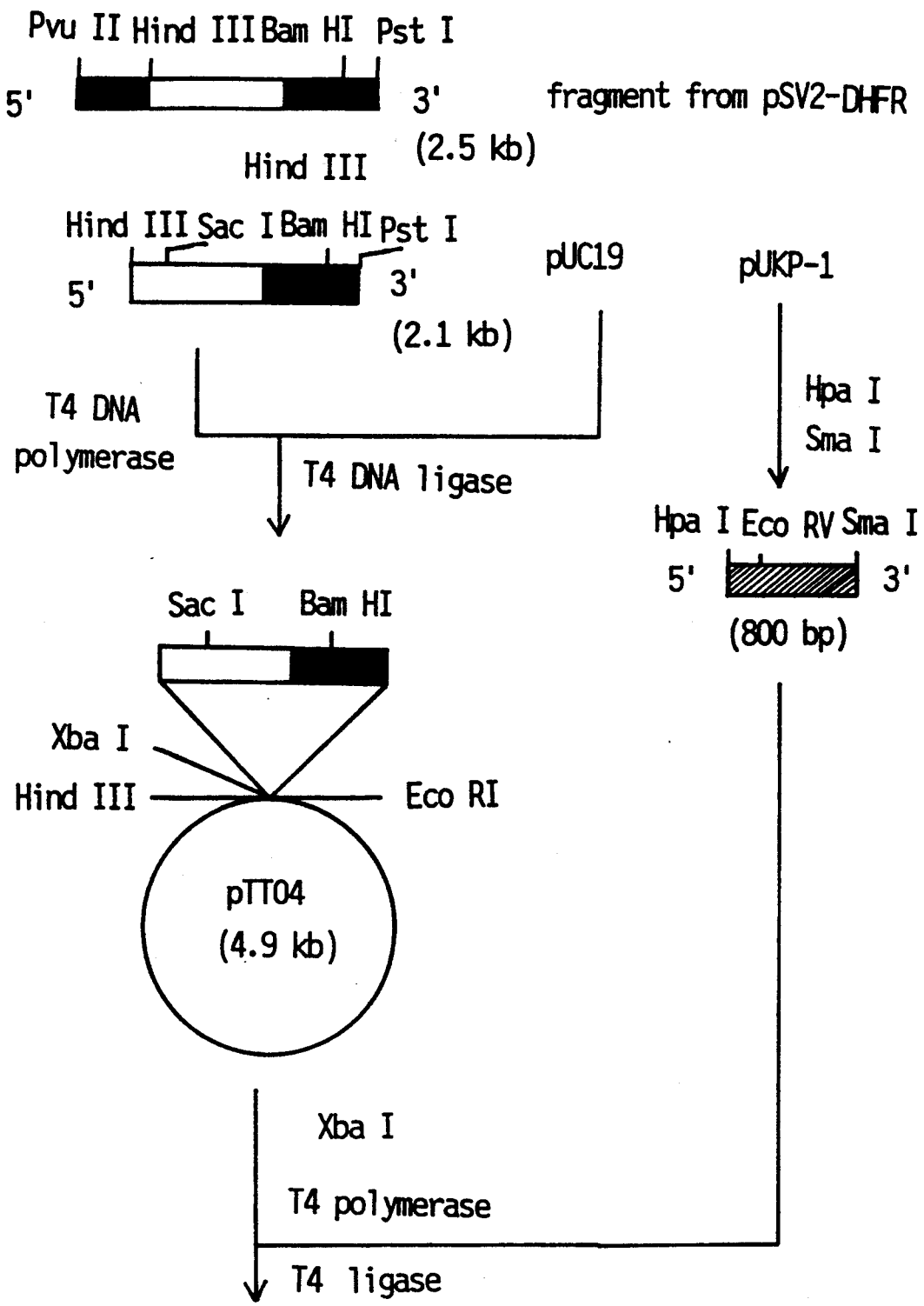
FIG. 11 shows the general construction steps of pTT06.
Figure 11B:
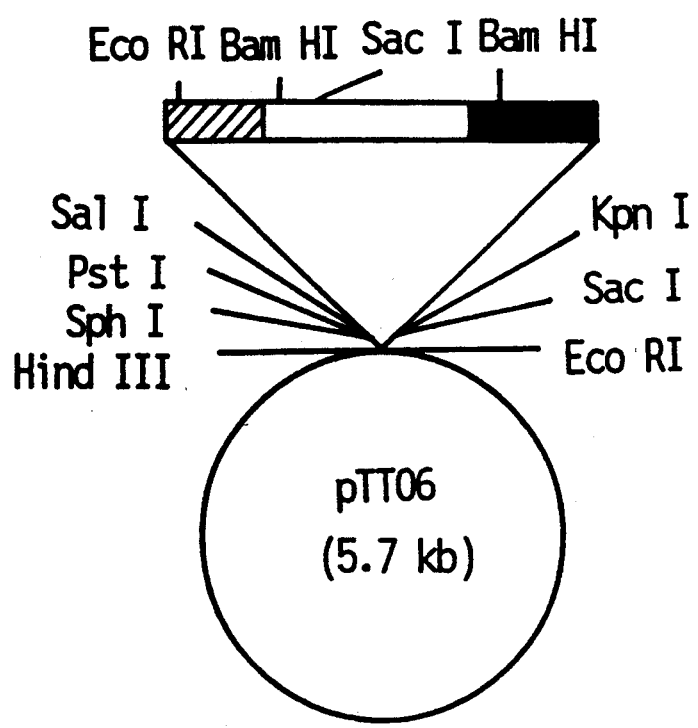

(ii) Construction of pTT06—Construction of plasmid containing UK promoter, DHFR cDNA, and SV40 poly A FIG. 11 shows the general flow of the plasmid construction. The DNA fragment containing SV40 enhancer-promoter, DHFR cDNA, and SV40 late poly A addition signal, and obtained by treating pSV2-DHFR (EP-A-265874) with PvuII and pstI was further cut with HindIII to give a 2.1 kb DNA fragment without the SV40 enhancer-promoter. This HindIII-PstI DNA fragment was given blunt end with T4 DNA polymerase, and cloned at the SmaI cleavage site of pUC19 (Takara Shuzo, Japan), whereby there was obtained pTT04 wherein the 5' end (N terminal of protein) of DHFR cDNA faces HindIII in the polylinker of pUC19. Confirmation of plasmid was conducted by the size of the DNA fragments cleaved out by BamHI digestion with BamHI in the polylinker of pUC19, and BamHI located at the downstream of SV40 poly A addition signal. A 1.6 kb DNA fragment was obtained from pTT04. Then, pUKP-1 was cut with HpaI and SmaI, and about 800 bp DNA fragment cleaved out from the SmaI recognition site at about 30 bp downstream from the urokinase gene transcription initiation codon, and HpaI recognition site at about 800 bp upstream from the transcription initiation codon was obtained. This DNA fragment containing UK promoter site was inserted into the upstream of DHFR cDNA of pTT04. That is, after digestion of pTT04 with XbaI, it was subjected to BAP treatment, given blunt end with T4 DNA polymerase, and ligated with HpaI-SmaI fragment of UK promoter. After transformation, a clone having DHFR gene and UK promoter facing the same transcription direction was selected from the colonies obtained. A plasmid giving a 280 bp DNA fragment by cleavage with EcoRV whose recognition site is located near 5' end of UK promoter, and Sal I in pUC19 was selected and named pTT06. The structure of the plasmid was confirmed by the cleavage with EcoRV-+SacI, and EcoRV+BamHI. By the digestion of pTT06 with EcoRV and SacI, 0.9, 1.8, and 2.9 kb fragments were obtained, and by the digestion with BamHI, 0.6, 1.6, and 3.5 kb fragments were obtained. The size of these fragments coincided with that in the restriction enzyme map of the objective plasmid.

What is claimed is:

1. An isolated mutant human prourokinase, wherein in the epidermal growth factor region from the Asn (10) to the Thr (49) of the human prourokinase shown in SEQ ID No: 7, at least one of Gly (16) in the amino acid sequence of human prourokinase is substituted with a Lys residue and Gly (38) in the amino acid sequence of human prourokinase is substituted with a Lys residue.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i x ) FEATURE:
        ( A ) NAME/KEY: CDS
        ( B ) LOCATION: 1..33

( x i ) SEQUENCE DESCRIPTION: SEQ ID NO:1:

```
GAC TGT CTA AAT GGA GGA ACA TGT GTG TCC AAC              33
Asp Cys Leu Asn Gly Gly Thr Cys Val Ser Asn
 1               5                       10
```

( 2 ) INFORMATION FOR SEQ ID NO:2:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( x i ) SEQUENCE DESCRIPTION: SEQ ID NO:2:

```
ACTGTCTAAA TAAAGGTACC TGTGTGTCCA AC                      32
```

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i x ) FEATURE:
        ( A ) NAME/KEY: CDS
        ( B ) LOCATION: 1..36

( x i ) SEQUENCE DESCRIPTION: SEQ ID NO:3:

```
AAC TGC CCA AAG AAA TTC GGA GGG CAG CAC TGT GAA          36
Asn Cys Pro Lys Lys Phe Gly Gly Gln His Cys Glu
 1               5                       10
```

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( x i ) SEQUENCE DESCRIPTION: SEQ ID NO:4:

```
CTGTCCAAAG AAATTTAAAG GGCAGCACTG TGA                     33
```

( 2 ) INFORMATION FOR SEQ ID NO:5:

( i ) SEQUENCE CHARACTERISTICS:

(A) LENGTH: 45 base pairs
(B) TYPE: nucleic acid
(C) STRANDEDNESS: single
(D) TOPOLOGY: linear (ii) MOLECULE TYPE: other nucleic acid
(A) DESCRIPTION: synthetic DNA (ix) FEATURE:
(A) NAME/KEY: CDS
(B) LOCATION: 1..45

(xi) SEQUENCE DESCRIPTION: SEQ ID NO:5:

| CAG | CAC | TGT | GAA | ATA | GAT | AAG | TCA | AAA | ACC | TGC | TAT | GAG | GGG | AAT | 45 |
|---|---|---|---|---|---|---|---|---|---|---|---|---|---|---|---|
| Gln | His | Cys | Glu | Ile | Asp | Lys | Ser | Lys | Thr | Cys | Tyr | Glu | Gly | Asn | |
| 1 | | | | 5 | | | | | 10 | | | | | 15 | |

(2) INFORMATION FOR SEQ ID NO:6:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: other nucleic acid
(A) DESCRIPTION: synthetic DNA (xi) SEQUENCE DESCRIPTION: SEQ ID NO:6:

CAGCACTGTG AAATTAATAA GTCAAAAACA TGTTATGAGG GGAAT          45

(2) INFORMATION FOR SEQ ID NO:7:

(i) SEQUENCE CHARACTERISTICS:
(A) LENGTH: 1236 base pairs
(B) TYPE: nucleic acid
(C) STRANDEDNESS: double
(D) TOPOLOGY: both (ii) MOLECULE TYPE: DNA (genomic)

(vi) ORIGINAL SOURCE:
(C) INDIVIDUAL ISOLATE: human (ix) FEATURE:
(A) NAME/KEY: CDS
(B) LOCATION: 1..1233

(xi) SEQUENCE DESCRIPTION: SEQ ID NO:7:

| AGC | AAT | GAA | CTT | CAT | CAA | GTT | CCA | TCG | AAC | TGT | GAC | TGT | CTA | AAT | GGA | 48 |
|---|---|---|---|---|---|---|---|---|---|---|---|---|---|---|---|---|
| Ser | Asn | Glu | Leu | His | Gln | Val | Pro | Ser | Asn | Cys | Asp | Cys | Leu | Asn | Gly | |
| 1 | | | | 5 | | | | | 10 | | | | | 15 | | |

| GGA | ACA | TGT | GTG | TCC | AAC | AAG | TAC | TTC | TCC | AAC | ATT | CAC | TGG | TGC | AAC | 96 |
|---|---|---|---|---|---|---|---|---|---|---|---|---|---|---|---|---|
| Gly | Thr | Cys | Val | Ser | Asn | Lys | Tyr | Phe | Ser | Asn | Ile | His | Trp | Cys | Asn | |
| | | | 20 | | | | | 25 | | | | | 30 | | | |

| TGC | CCA | AAG | AAA | TTC | GGA | GGG | CAG | CAC | TGT | GAA | ATA | GAT | AAG | TCA | AAA | 144 |
|---|---|---|---|---|---|---|---|---|---|---|---|---|---|---|---|---|
| Cys | Pro | Lys | Lys | Phe | Gly | Gly | Gln | His | Cys | Glu | Ile | Asp | Lys | Ser | Lys | |
| | | 35 | | | | | 40 | | | | | 45 | | | | |

| ACC | TGC | TAT | GAG | GGG | AAT | GGT | CAC | TTT | TAC | CGA | GGA | AAG | GCC | AGC | ACT | 192 |
|---|---|---|---|---|---|---|---|---|---|---|---|---|---|---|---|---|
| Thr | Cys | Tyr | Glu | Gly | Asn | Gly | His | Phe | Tyr | Arg | Gly | Lys | Ala | Ser | Thr | |
| | 50 | | | | | 55 | | | | | 60 | | | | | |

| GAC | ACC | ATG | GGC | CGG | CCC | TGC | CTG | CCC | TGG | AAC | TCT | GCC | ACT | GTC | CTT | 240 |
|---|---|---|---|---|---|---|---|---|---|---|---|---|---|---|---|---|
| Asp | Thr | Met | Gly | Arg | Pro | Cys | Leu | Pro | Trp | Asn | Ser | Ala | Thr | Val | Leu | |
| 65 | | | | | 70 | | | | | 75 | | | | | 80 | |

| CAG | CAA | ACG | TAC | CAT | GCC | CAC | AGA | TCT | GAT | GCT | CTT | CAG | CTG | GGC | CTG | 288 |
|---|---|---|---|---|---|---|---|---|---|---|---|---|---|---|---|---|
| Gln | Gln | Thr | Tyr | His | Ala | His | Arg | Ser | Asp | Ala | Leu | Gln | Leu | Gly | Leu | |
| | | | | 85 | | | | | 90 | | | | | 95 | | |

| GGG | AAA | CAT | AAT | TAC | TGC | AGG | AAC | CCA | GAC | AAC | CGG | AGG | CGA | CCC | TGG | 336 |
|---|---|---|---|---|---|---|---|---|---|---|---|---|---|---|---|---|
| Gly | Lys | His | Asn | Tyr | Cys | Arg | Asn | Pro | Asp | Asn | Arg | Arg | Arg | Pro | Trp | |
| | | | 100 | | | | | 105 | | | | | 110 | | | |

| | | | | | | | | | | | | | | | | |
|---|---|---|---|---|---|---|---|---|---|---|---|---|---|---|---|---|
| TGC | TAT | GTG | CAG | GTG | GGC | CTA | AAG | CCG | CTT | GTC | CAA | GAG | TGC | ATG | GTG | 384 |
| Cys | Tyr | Val 115 | Gln | Val | Gly | Leu | Lys 120 | Pro | Leu | Val | Gln | Glu 125 | Cys | Met | Val | |
| CAT | GAC | TGC | GCA | GAT | GGA | AAA | AAG | CCC | TCC | TCT | CCT | CCA | GAA | GAA | TTA | 432 |
| His | Asp 130 | Cys | Ala | Asp | Gly | Lys | Lys 135 | Pro | Ser | Ser | Pro | Pro 140 | Glu | Glu | Leu | |
| AAA | TTT | CAG | TGT | GGC | CAA | AAG | ACT | CTG | AGG | CCC | CGC | TTT | AAG | ATT | ATT | 480 |
| Lys 145 | Phe | Gln | Cys | Gly | Gln 150 | Lys | Thr | Leu | Arg | Pro 155 | Arg | Phe | Lys | Ile | Ile 160 | |
| GGG | GGA | GAA | TTC | ACC | ACC | ATC | GAG | AAC | CAG | CCC | TGG | TTT | GCG | GCC | ATC | 528 |
| Gly | Gly | Glu | Phe | Thr 165 | Thr | Ile | Glu | Asn | Gln 170 | Pro | Trp | Phe | Ala | Ala 175 | Ile | |
| TAC | AGG | AGG | CAC | CGG | GGG | GGC | TCT | GTC | ACC | TAC | GTG | TGT | GGA | GGC | AGC | 576 |
| Tyr | Arg | Arg | His 180 | Arg | Gly | Gly | Ser | Val 185 | Thr | Tyr | Val | Cys | Gly 190 | Gly | Ser | |
| CTC | ATC | AGC | CCT | TGC | TGG | GTG | ATC | AGC | GCC | ACA | CAC | TGC | TTC | ATT | GAT | 624 |
| Leu | Ile | Ser 195 | Pro | Cys | Trp | Val | Ile 200 | Ser | Ala | Thr | His | Cys 205 | Phe | Ile | Asp | |
| TAC | CCA | AAG | AAG | GAG | GAC | TAC | ATC | GTC | TAC | CTG | GGT | CGC | TCA | AGG | CTT | 672 |
| Tyr | Pro 210 | Lys | Lys | Glu | Asp | Tyr 215 | Ile | Val | Tyr | Leu | Gly 220 | Arg | Ser | Arg | Leu | |
| AAC | TCC | AAC | ACG | CAA | GGG | GAG | ATG | AAG | TTT | GAG | GTG | GAA | AAC | CTC | ATC | 720 |
| Asn 225 | Ser | Asn | Thr | Gln | Gly 230 | Glu | Met | Lys | Phe | Glu 235 | Val | Glu | Asn | Leu | Ile 240 | |
| CTA | CAC | AAG | GAC | TAC | AGC | GCT | GAC | ACG | CTT | GCT | CAC | CAC | AAC | GAC | ATT | 768 |
| Leu | His | Lys | Asp | Tyr 245 | Ser | Ala | Asp | Thr | Leu 250 | Ala | His | His | Asn | Asp 255 | Ile | |
| GCC | TTG | CTG | AAG | ATC | CGT | TCC | AAG | GAG | GGC | AGG | TGT | GCG | CAG | CCA | TCC | 816 |
| Ala | Leu | Leu | Lys 260 | Ile | Arg | Ser | Lys | Glu 265 | Gly | Arg | Cys | Ala | Gln 270 | Pro | Ser | |
| CGG | ACT | ATA | CAG | ACC | ATC | TGC | CTG | CCC | TCG | ATG | TAT | AAC | GAT | CCC | CAG | 864 |
| Arg | Thr | Ile 275 | Gln | Thr | Ile | Cys | Leu 280 | Pro | Ser | Met | Tyr | Asn 285 | Asp | Pro | Gln | |
| TTT | GGC | ACA | AGC | TGT | GAG | ATC | ACT | GGC | TTT | GGA | AAA | GAG | AAT | TCT | ACC | 912 |
| Phe | Gly | Thr 290 | Ser | Cys | Glu | Ile | Thr 295 | Gly | Phe | Gly | Lys | Glu 300 | Asn | Ser | Thr | |
| GAC | TAT | CTC | TAT | CCG | GAG | CAG | CTG | AAG | ATG | ACT | GTT | GTG | AAG | CTG | ATT | 960 |
| Asp | Tyr | Leu 305 | Tyr | Pro | Glu | Gln | Leu 310 | Lys | Met | Thr | Val | Val 315 | Lys | Leu | Ile 320 | |
| TCC | CAC | CGG | GAG | TGT | CAG | CAG | CCC | CAC | TAC | TAC | GGC | TCT | GAA | GTC | ACC | 1008 |
| Ser | His | Arg | Glu | Cys 325 | Gln | Gln | Pro | His | Tyr 330 | Tyr | Gly | Ser | Glu | Val 335 | Thr | |
| ACC | AAA | ATG | CTG | TGT | GCT | GCT | GAC | CCA | CAG | TGG | AAA | ACA | GAT | TCC | TGC | 1056 |
| Thr | Lys | Met | Leu 340 | Cys | Ala | Ala | Asp | Pro 345 | Gln | Trp | Lys | Thr | Asp 350 | Ser | Cys | |
| CAG | GGA | GAC | TCA | GGG | GGA | CCC | CTC | GTC | TGT | TCC | CTC | CAA | GGC | CGC | ATG | 1104 |
| Gln | Gly | Asp | Ser 355 | Gly | Gly | Pro | Leu | Val 360 | Cys | Ser | Leu | Gln | Gly 365 | Arg | Met | |
| ACT | TTG | ACT | GGA | ATT | GTG | AGC | TGG | GGC | CGT | GGA | TGT | GCC | CTG | AAG | GAC | 1152 |
| Thr | Leu | Thr 370 | Gly | Ile | Val | Ser | Trp 375 | Gly | Arg | Gly | Cys | Ala 380 | Leu | Lys | Asp | |
| AAG | CCA | GGC | GTC | TAC | ACG | AGA | GTC | TCA | CAC | TTC | TTA | CCC | TGG | ATC | CGC | 1200 |
| Lys | Pro 385 | Gly | Val | Tyr | Thr | Arg 390 | Val | Ser | His | Phe | Leu 395 | Pro | Trp | Ile | Arg 400 | |
| AGT | CAC | ACC | AAG | GAA | GAG | AAT | GGC | CTG | GCC | CTC | TGA | | | | | 1236 |
| Ser | His | Thr | Lys | Glu 405 | Glu | Asn | Gly | Leu | Ala 410 | Leu | | | | | | |

( 2 ) INFORMATION FOR SEQ ID NO:8:

( i ) SEQUENCE CHARACTERISTICS:
( A ) LENGTH: 33 base pairs
( B ) TYPE: nucleic acid ( C ) STRANDEDNESS: single
( D ) TOPOLOGY: linear ( i i ) MOLECULE TYPE: other nucleic acid
( A ) DESCRIPTION: synthetic DNA ( x i ) SEQUENCE DESCRIPTION: SEQ ID NO:8:

CTGCCCAAAG AAATTTAAAG GGCAGCACTG TGA 33